(12) United States Patent
Lane et al.

(10) Patent No.: US 10,702,147 B2
(45) Date of Patent: Jul. 7, 2020

(54) METHOD AND APPARATUS FOR CONTROLLING ACCOMMODATION AND PUPIL SIZE DURING AN EYE EXAMINATION

(71) Applicant: Welch Allyn, Inc., Skaneateles Falls, NY (US)

(72) Inventors: John A. Lane, Weedsport, NY (US); David L. Kellner, Baldwinsville, NY (US); Eric Joseph Laurin, Beaverton, OR (US); Zachary K. Boronka, Camillus, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 250 days.

(21) Appl. No.: 15/993,910

(22) Filed: May 31, 2018

(65) Prior Publication Data

US 2019/0313896 A1    Oct. 17, 2019

Related U.S. Application Data

(60) Provisional application No. 62/661,772, filed on Apr. 24, 2018, provisional application No. 62/658,003, filed on Apr. 16, 2018.

(51) Int. Cl.
*A61B 3/10* (2006.01)
*A61B 3/103* (2006.01)
(Continued)

(52) U.S. Cl.
CPC ............ *A61B 3/103* (2013.01); *A61B 3/0008* (2013.01); *A61B 3/15* (2013.01); *A61B 3/18* (2013.01); *A61B 3/0083* (2013.01)

(58) Field of Classification Search
CPC . A61B 1/00186; A61B 1/0638; A61B 1/0646; A61B 5/163; A61B 1/0684; A61B 3/0008; A61B 5/0261
(Continued)

(56) References Cited

U.S. PATENT DOCUMENTS 2,536,305 A   1/1951  Horton
7,427,135 B2  9/2008  Chen et al.
(Continued)

FOREIGN PATENT DOCUMENTS

WO    2013074232 A1    5/2013

OTHER PUBLICATIONS

An infrared eccentric photo-optometer; Vision Research 38 (1998) 1913-1924; Pergamon; Austin Roorda, William R. Bobier, Melanie C.W. Campbell; School of Optometry, University of Waterloo, Waterloo, Ontario, Canada N2L 3G1, received in revised form Sep. 27, 1997; (c) 1998 Elsevier Science Ltd. All rights reserved. PII: S0042-6989(97)00424-0; 12-pages.
(Continued)

*Primary Examiner* — Hung X Dang
(74) *Attorney, Agent, or Firm* — Kenneth L. Lilly

(57) ABSTRACT

A system for conducting an examination of the eyes of a subject includes an examination instrument which emits light at infrared wavelengths, and a shield. The shield provides shielding of the subject's eyes from visible wavelengths. At least a portion of the shield is transparent to the infrared wavelengths emitted by the examination instrument. A related method of conducting an eye examination on a subject includes the step of providing a shield which is transparent to infrared wavelengths but nontransparent to visible wavelengths. The method also includes the step of carrying out the examination with an instrument which is located on the examiner facing side of the shield and which
(Continued)

emits the infrared wavelengths to which the shield is transparent. One variant of the method determines parameters relating to the subject's eyes and/or vision using only information considered to be valid, validity being based on the subject's pupil diameter.

22 Claims, 22 Drawing Sheets

(51) Int. Cl.
  *A61B 3/00* (2006.01)
  *A61B 3/18* (2006.01)
  *A61B 3/15* (2006.01)
(58) Field of Classification Search
  USPC .......................................... 351/221, 246, 205
  See application file for complete search history.

(56) References Cited

U.S. PATENT DOCUMENTS

| 8,323,216 | B2 | 12/2012 | Fabian |
| 8,494,229 | B2* | 7/2013 | Jarvenpaa ............... A61B 3/113 382/117 |
| 9,237,846 | B2 | 1/2016 | Mowrey et al. |
| 9,237,847 | B2 | 1/2016 | Wang et al. |
| 9,269,330 | B2 | 2/2016 | Yang |
| 9,402,538 | B2 | 8/2016 | Mowrey et al. |
| 9,408,535 | B2 | 8/2016 | Mowrey et al. |
| 2005/0231688 | A1 | 10/2005 | Jones et al. |
| 2014/0336723 | A1 | 11/2014 | Ben-Ezra et al. |
| 2016/0270656 | A1 | 9/2016 | Samec et al. |

OTHER PUBLICATIONS

Dynamic Retinoscopy Methods; Dec. 10, 2016; by Sushma (http://optometryzone.com/author/sushma/); Mar. 14, 2018; 5-pages.
Measuring eccentric photo refraction with accomodation and pupil control using a tinted medium; Mar. 2018; D Kellner, E Laurin, J Lane; 5-pages.
Opthalmic Technician.org; Resources for opthalmic medical personnel Opthalmic Assistants Opthalmic Technicians Opthalmic Technologist; To fog or not to fog? 4-pages; http://www.opthalmictechnician.org/index.php/techh-tips/160-to-fog-or-not-to-fog; Mar. 14, 2018.
Vision Screener since 2001 plusoptix; made in Germany; plusoptix.com; Version Sep. 12, 2017.

* cited by examiner

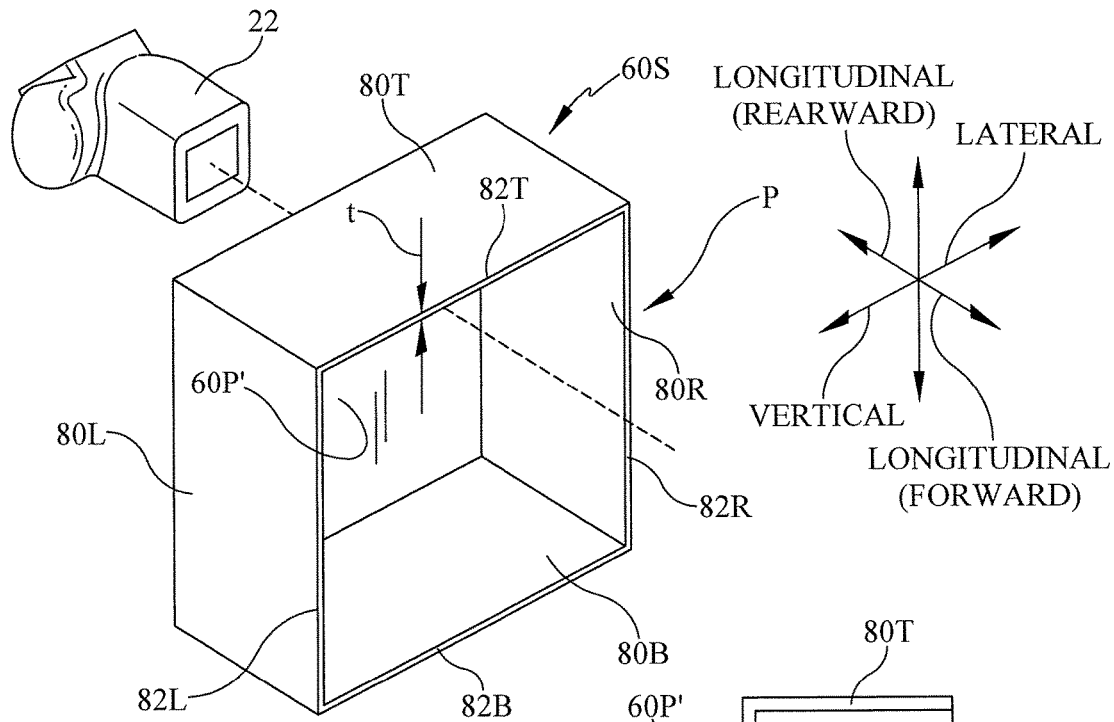
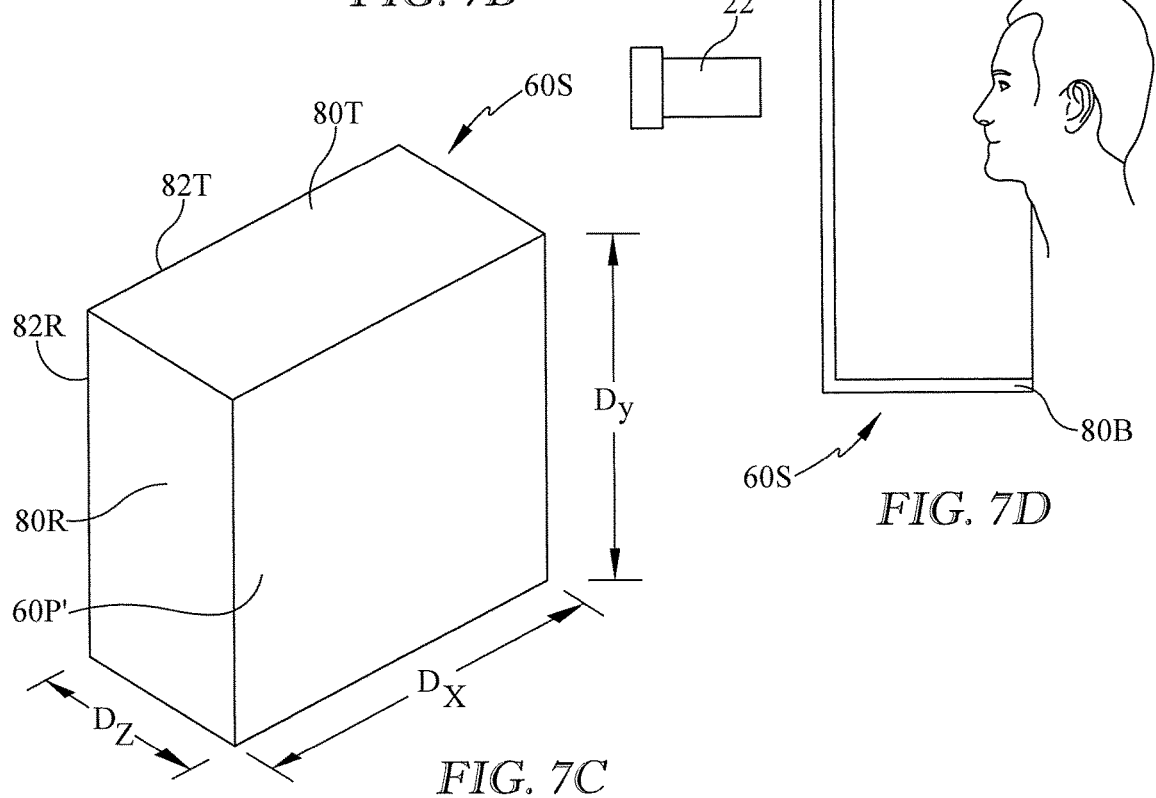

METHOD AND APPARATUS FOR CONTROLLING ACCOMMODATION AND PUPIL SIZE DURING AN EYE EXAMINATION

CROSS-REFERENCE TO RELATED PATENT APPLICATIONS

This application claims priority to U.S. Provisional Applications 62/661,772 filed on Apr. 24, 2018 and 62/658,003 filed on Apr. 16, 2018 the contents of both of which are incorporated herein by reference.

TECHNICAL FIELD

The subject matter described herein relates to eye examinations and particularly to an apparatus and method for controlling accommodation and pupil size during examination of a subject's eyes by an eye examination instrument.

BACKGROUND

Eye examinations are traditionally carried out in a well controlled environment, for example in an examination room in an optometrist's or ophthalmologist's office. In such environments the examiner can control lighting, distractions, and other influences that may compromise the accuracy of the examination. The examiner also has ample time to allow the examinee's eyes to adjust to changes in lighting.

Eye examinations are also carried out in less controlled environments. One example is a screening carried out on a large population of students in a school facility such as a gymnasium. The need to examine numerous students at a high tempo, and in relatively bright conditions is not inherently conducive to examination accuracy.

Another example is a retail outlet in a well lighted environment such as a shopping mall. If the outlet is not equipped with a controlled environment, the accuracy of the examination may suffer.

An additional difficulty arises if the examination requires the subject's eyes to be in a resting state of accommodation, which is a state in which there is no adequate stimulus for the subject's eyes to focus on. However in practice the subject may focus on the examiner or the examiner's equipment rather than maintain the desired resting state of accommodation. This difficulty can be especially prevalent when the subject is a child.

Therefore, there is a need to develop methods and equipment which enable an examiner to carry out an accurate vision examination in environments which are not well controlled and in which the subject may be unable or unwilling to maintain his eyes in a resting state of accommodation.

SUMMARY

The present invention may comprise one or more of the features recited in the appended claims and/or one or more of the following features or combinations thereof.

A system for conducting an examination of the eyes of a subject includes an examination instrument which emits light at infrared wavelengths and a shield. The shield provides shielding of the subject's eyes from visible wavelengths. At least a portion of the shield is transparent to the infrared wavelengths emitted by the examination instrument.

A method of conducting an eye examination on a subject includes the step of providing a shield which is transparent to infrared wavelengths but nontransparent to visible wavelengths. The method also includes the step of carrying out the examination with an instrument which is located on the examiner facing side of the shield and which emits the infrared wavelengths to which the shield is transparent.

BRIEF DESCRIPTION OF THE DRAWINGS

The foregoing and other features of the various embodiments of the eye examination systems and methods described herein will become more apparent from the following detailed description and the accompanying drawings in which:

FIGS. 7B and 7C are schematic perspective views of a shield component of the eye examination system in which the shield is in the form of a shadowbox having top, bottom, left, and right panels which block visible wavelengths and having a rearward panel at least part of which is transparent to infrared wavelengths.

FIG. 7D is a cross sectional side elevation view of the shadowbox of FIGS. 7A and 7B.

DESCRIPTION

Figure 1:
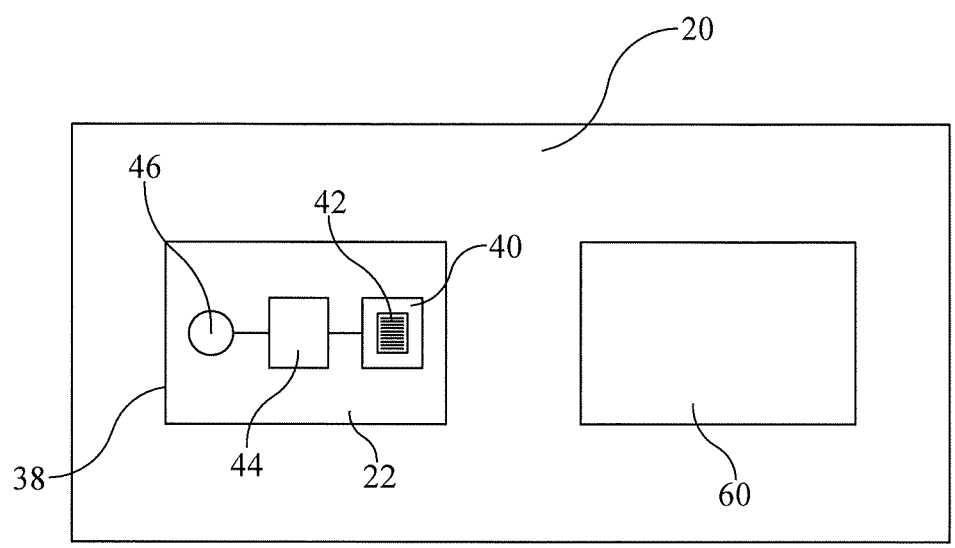
FIG. 1 is a schematic view of an eye examination system comprised of an examination instrument and a shield for carrying out a vision screening on a subject.

In this specification and drawings, features similar to or the same as features already described may be identified by reference characters or numerals which are the same as or similar to those previously used. Similar elements may be identified by a common reference character or numeral, with suffixes being used to refer to specific occurrences of the element.

FIG. 1 shows a system 20 for examining the eyesight of a subject. System 20 includes an eye examination instrument 22 and a shield 60.

Figure 2:
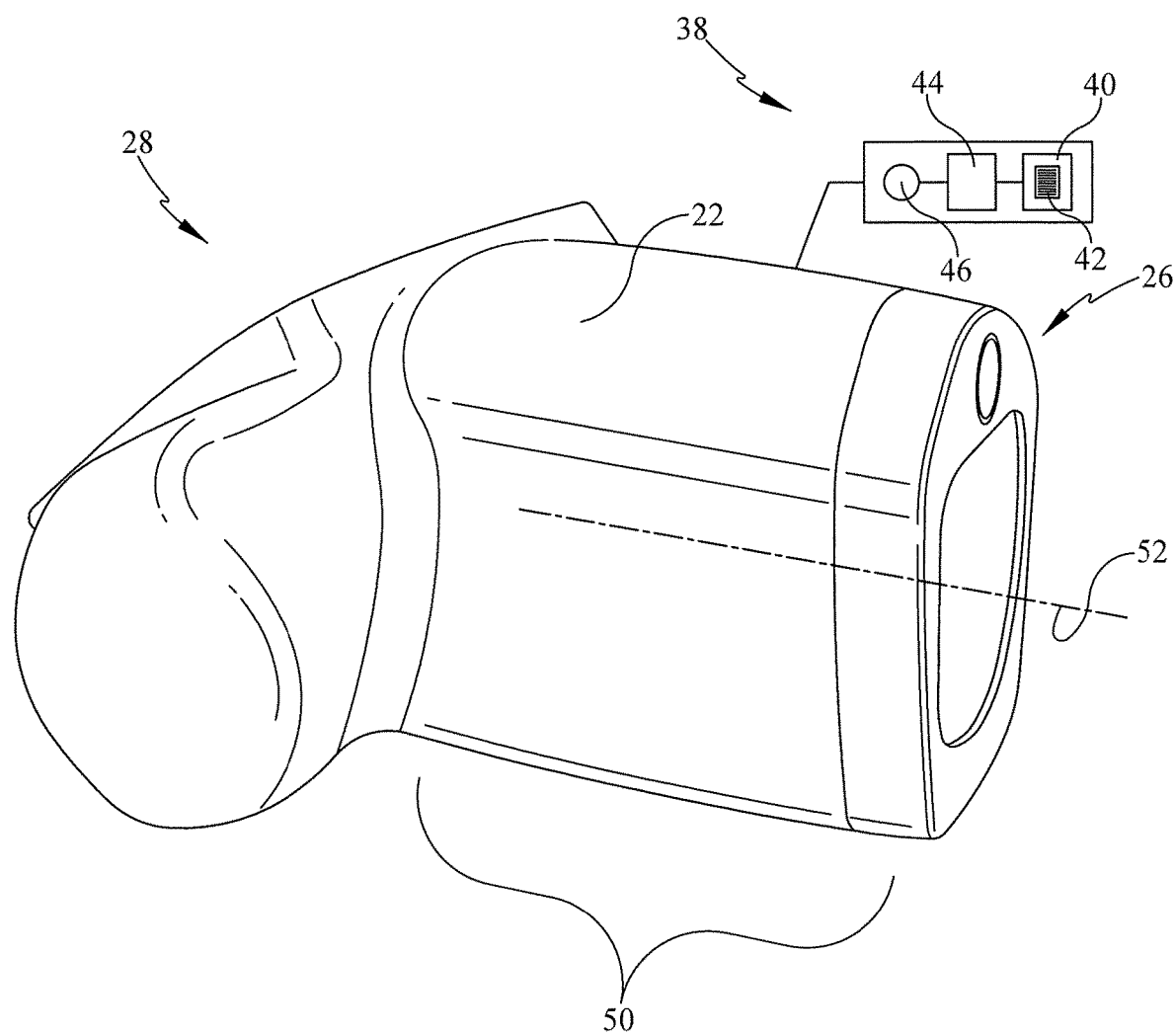
FIG. 2 is a view of a commercially available examination instrument, specifically an eccentric photorefractor (EPR), oriented so that the examiner end of the EPR is at the left of the illlustration and the subject end of the EPR is at the right of the illustration.
Figure 3:
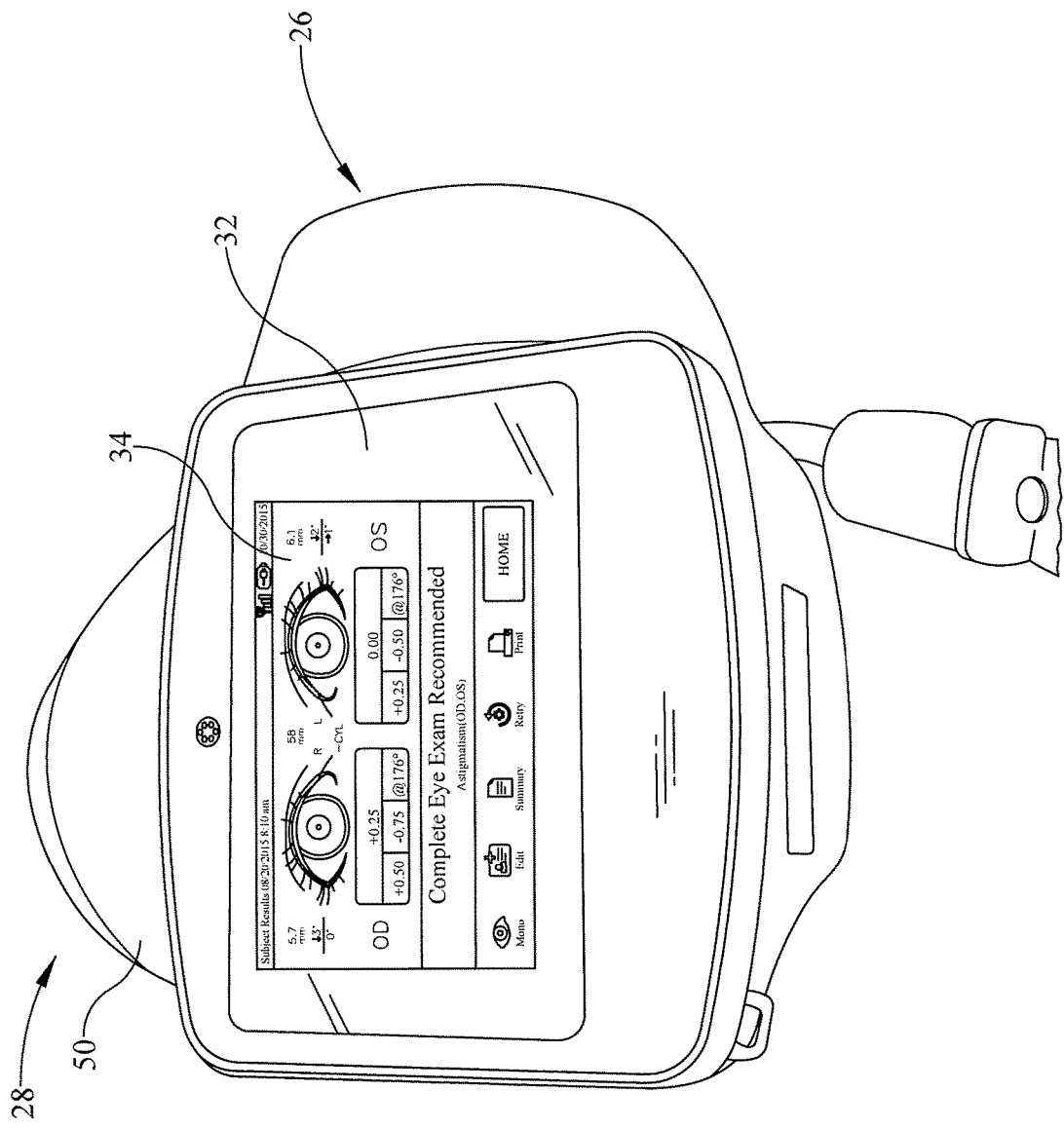
FIG. 3 is a view of the EPR of FIG. 2 from the examiner side thereof showing a display and information displayed on the display.
Figure 4:
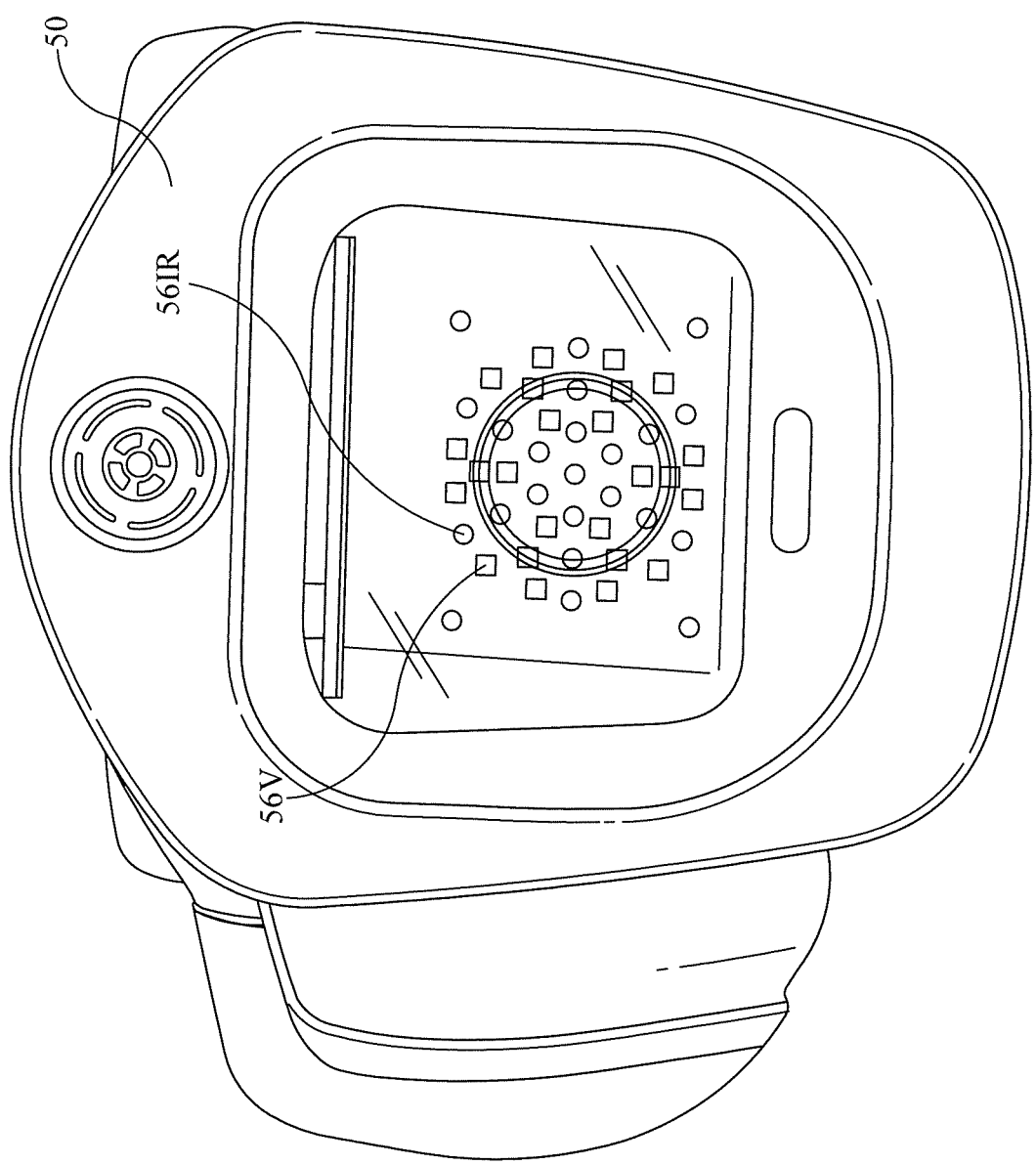
FIG. 4 is a view of the EPR of FIGS. 2 and 3 from the subject side thereof showing visible and infrared light emitters recessed in a barrel of the EPR.

Referring to FIGS. 2-4, the illustrated examination instrument 22 is model VS100 eccentric photorefractor (EPR) vision screener obtainable from Welch Allyn® 4341 State St., Skaneateles Falls, N.Y., United States 13151, and marketed under the name Welch Allyn® Spot® Vision Screener. Other vision examination instruments may also be suitable components of examination system 20.

Vision screener 22 extends longitudinally from a subject end 26 to an examiner end 28. The screener includes a display 32 such as a liquid crystal display screen (LCD). for displaying information 34 to the examiner. In FIG. 3 the LCD is displaying results from an examination conducted with the vision screener, including a recommendation that the examinee undergo a more complete examination. As shown schematically in FIGS. 1 and 2, the vision screener also includes a camera system 38 which includes optical sensors 46. The vision screener also includes a memory 40 with machine readable instructions 42, and a processor 44 which carries out the instructions. The processor, acting according to the instructions, controls the functions of the screener, including the camera system. The instructions may include a variety of instruction subsets or subroutines adapted for different tasks or different situations.

The vision screener 22 also includes a barrel 50 having an axis 52, and an array of emitters 56 inside the barrel. The emitters are recessed away from the subject end 26 of the barrel. A first subset 56V of the emitters is configured to emit light at blue wavelengths in the visible portion of the electromagnetic spectrum. A second subset 56IR of the emitters is configured to emit light at infrared wavelengths, for example at a central wavelength of about 850 nanometers. As indicated by the foregoing, "light" is used herein to refer to both the visible portion of the spectrum as well as to nonvisible portions of the spectrum. A distance sensor 58, such as a sonar sensor detects the distance to the subject so that the screener operates only if that distance is within a prescribed range.

Figure 5:
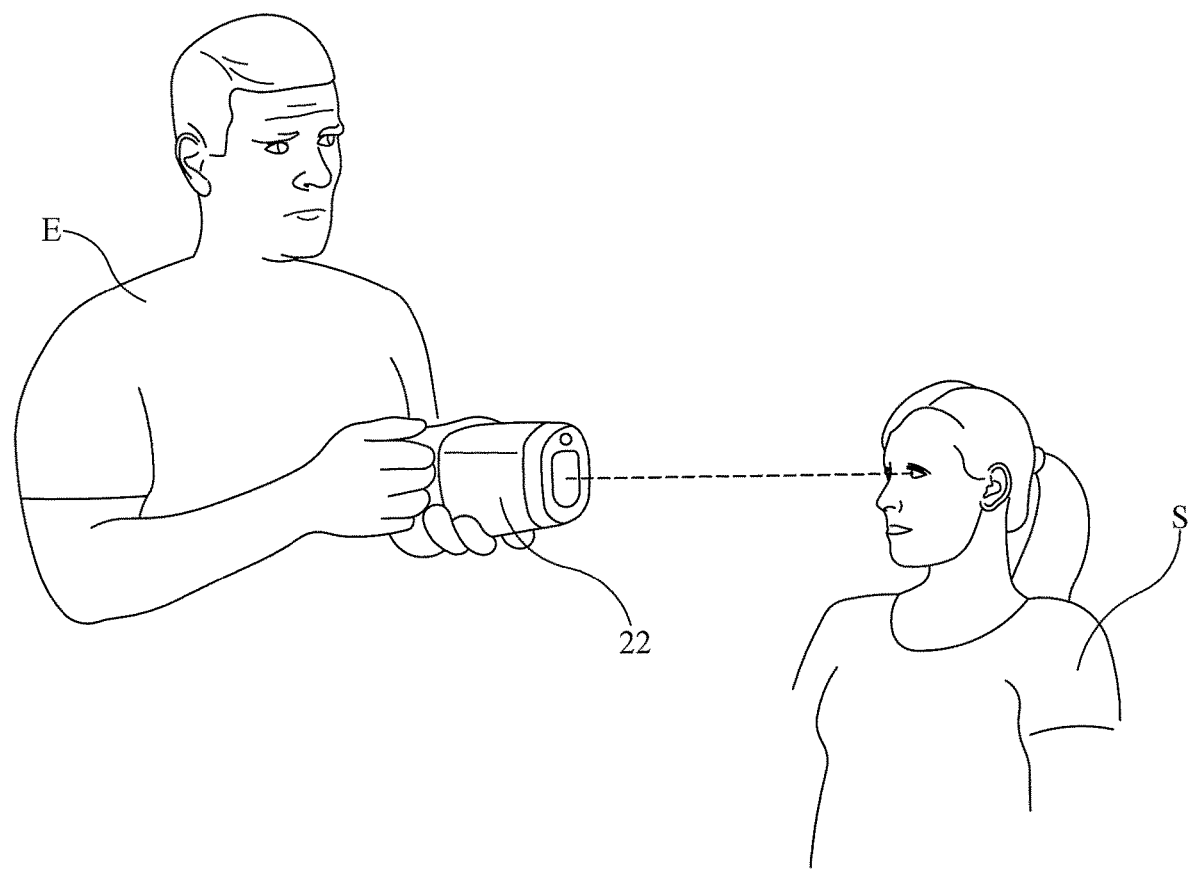
FIG. 5 is a view showing an examiner using an EPR to examine the eyes of a subject.

Referring to FIG. 5, in practice the examiner E maneuvers screener 22 until it is on-axis with the eyes of subject S and at the correct distance form the subject. Emitters 56V, 56IR emit flashes of blue and infrared light as well as an audible sound, such as the sound of birds chirping. The blue lights and chirping sounds attract the subject's attention so that he keeps his eyes on-axis with the screener for the duration of the examination. Infrared light refracted from the subject's eyes form an image in the plane of the subject's pupils. The image is captured by the screener and processed by processor 44 according to instructions 42 to evaluate the subject's vision.

The combination of the blue lights and the chirping sounds are useful for keeping the subject's eyes directed toward the vision screener as described above. However they also cause the subject's eyes to adjust from the resting state of accommodation required for good examination accuracy to a state of focus on the vision screener, including adjusting for any inherent refractive error of his eyes.

System 20 also includes a shield 60 to induce the desired resting state of accommodation. At least a portion of the shield is transparent to the infrared wavelengths emitted by emitters 56IR. The infrared transparency allows the infrared light emitted by photorefractor 22 to arrive at the subject's eyes and allows the infrared light refracted by the subject's eyes to arrive back at the photorefractor for processing by processor 44. However the shield also provides a degree of "on-demand" shielding of the subject's eyes from visible wavelengths and therefore guards against the possibility that the subject's eyes will not be in the desired resting state of accommodation. The shielding from visible wavelengths blocks the subject's view of objects to help induce the resting state of accommodation thereby increasing accuracy of the examination. As a practical matter it is not required that the shield be absolutely opaque to visible wavelengths. Accordingly, "opaque" and variants thereof in this specification mean that the shield is opaque enough to induce the desired resting state of accommodation.

Figure 6A:
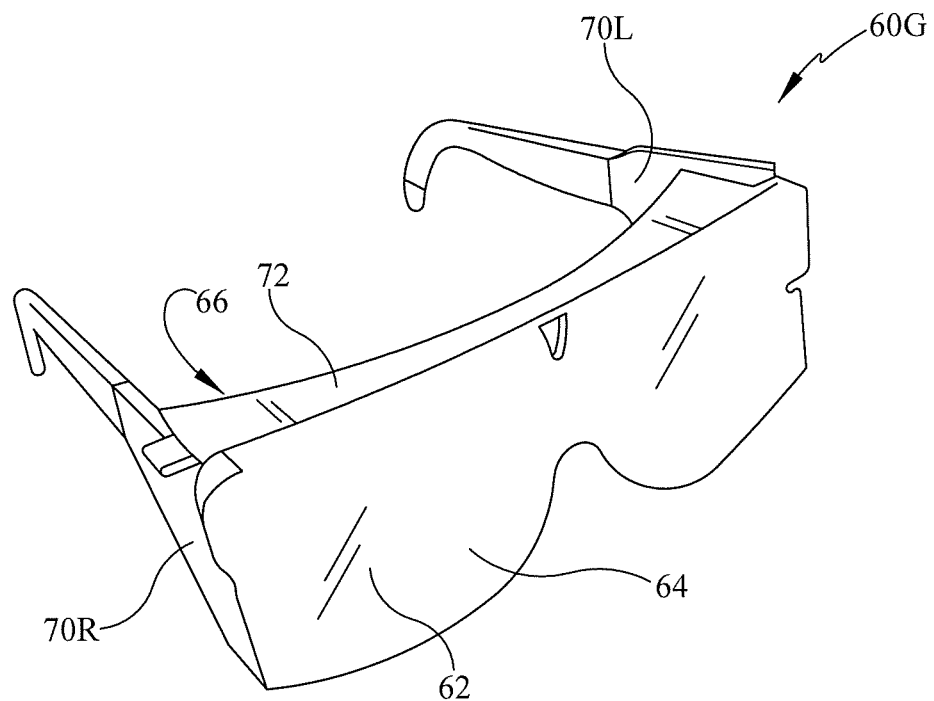
FIG. 6A is a view of a shield component of the eye examination system in which the shield is in the form of dark glasses which block visible light, but at least a portion of which is transparent to infrared wavelengths.
Figure 6B:
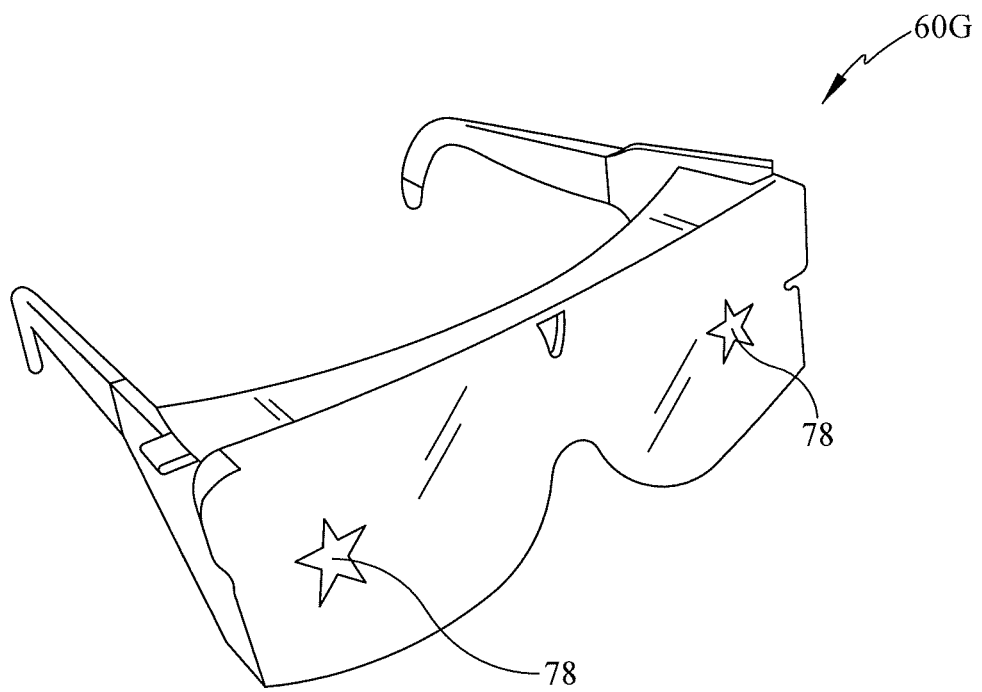
FIG. 6B is a view similar to FIG. 6A in which the glasses include a watermark.

Referring to FIGS. 6A and 6B, in one embodiment the shield is a pair of dark glasses 60G having a forward facing shield portion 62. In this specification, including the claims, the phrase "pair of glasses" is used in its common idiomatic sense in which "pair" does not mean "two". The shield portion has a subject facing side 64 and an examiner facing side 66. The illustrated glasses are of the "wrap-around" style and therefore also include side shield portions 70L, 70R. A top shield portion 72 spans across the top of the forward facing portion 62 from left side shield portion 70L to right side shield portion 70R. The dark tint of the forward facing portion blocks visible light. However at least part of forward facing portion is transparent to infrared wavelengths so that light at infrared wavelengths can propagate from the vision screener to the subject's eyes and vice versa. The side and top portions also block visible light and may or may not be transparent to infrared.

The embodiment of FIG. 6B is the same as that of FIG. 6A but also includes a mark 78 referred to as a watermark. The watermark of FIG. 6B is a star, however other forms of the watermark are satisfactory. Although the watermark is illustrated only in FIG. 6B, it is applicable to other embodiments of the shield. The significance of the watermark is described later in this specification.

Figure 7A:
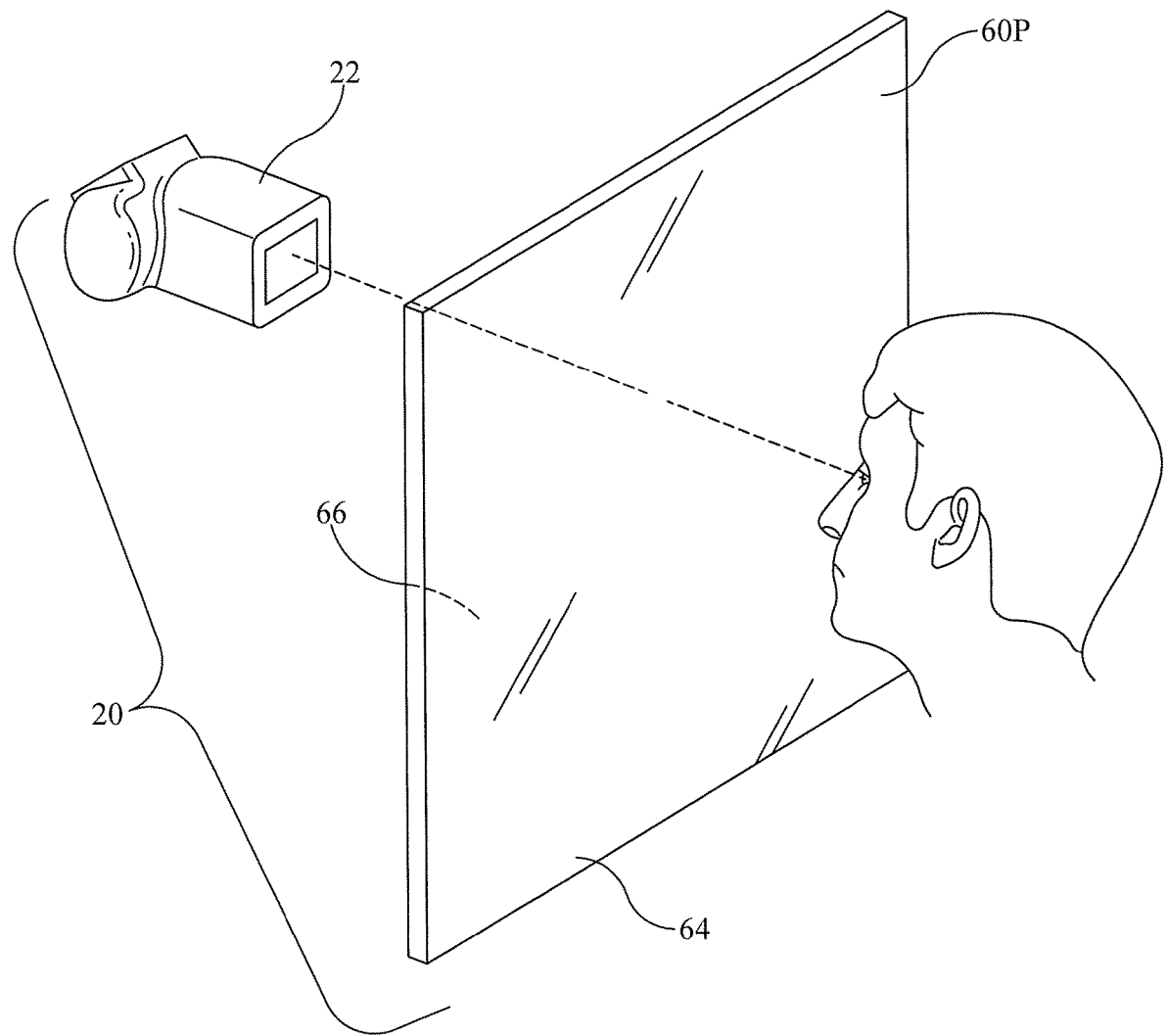
FIG. 7A is a view of a shield component of the eye examination system in which the shield is in the form of a pane of material which blocks visible light, but at least a portion of which is transparent to infrared wavelengths.

Referring to FIG. 7A, in another embodiment the shield is a pane 60P of material opaque to visible light. At least a portion of the pane is infrared transparent so that light at infrared wavelengths can propagate from the vision screener to the subject's eyes and vice versa. The illustrated pane 60P is planar, however the pane could instead be curved in two or three dimensions to better shield the subject's eyes from ambient visible light.

Referring to FIGS. 7B-7D, in yet another embodiment the shield is a shadowbox 60S having a top panel 80T, a bottom panel 80B, and laterally left and right side panels 80L, 80R. All four panels are opaque to visible light. In the illustrated embodiment forward edges 82T, 82B, 82L and 82R of the panels lie in a plane and define an opening 84. The shadowbox also includes an infrared transparent pane of material 60P' analogous to pane 60P of FIG. 7A. The pane is recessed longitudinally away from plane P, spans laterally between panels 80L and 80R, and spans vertically between panels 80T and 80B.

In one specific embodiment shadowbox dimensions $D_x$, $D_y$, are both about two feet (61 cm) and $D_z$ is about three feet (91 cm) in order to ensure that sonar reflections from panels 80 will not result in erroneous distance readings. In an alternate, more compact embodiment $D_x$ and $D_y$ are both about eighteen inches (46 cm) and $D_z$ is about 1 foot (30 cm). However the panel thickness t of the more compact embodiment is only about one sixteeenth of an inch (1.6 mm) to prevent sonar reflection. One material believed to be suitable for the panels is corrugated cardboard because the flutes of the cardboard are hollow and therefore the cardboard does not readily reflect back the sonar signal.

In practice the subject positions his face at or near plane P (including past plane P as seen best in FIG. 7D). The opacity of shadowbox panels 80T, 80B, 80L and 80R blocks the subject's view of objects thereby inducing the desired resting state of accommodation.

Figure 8:
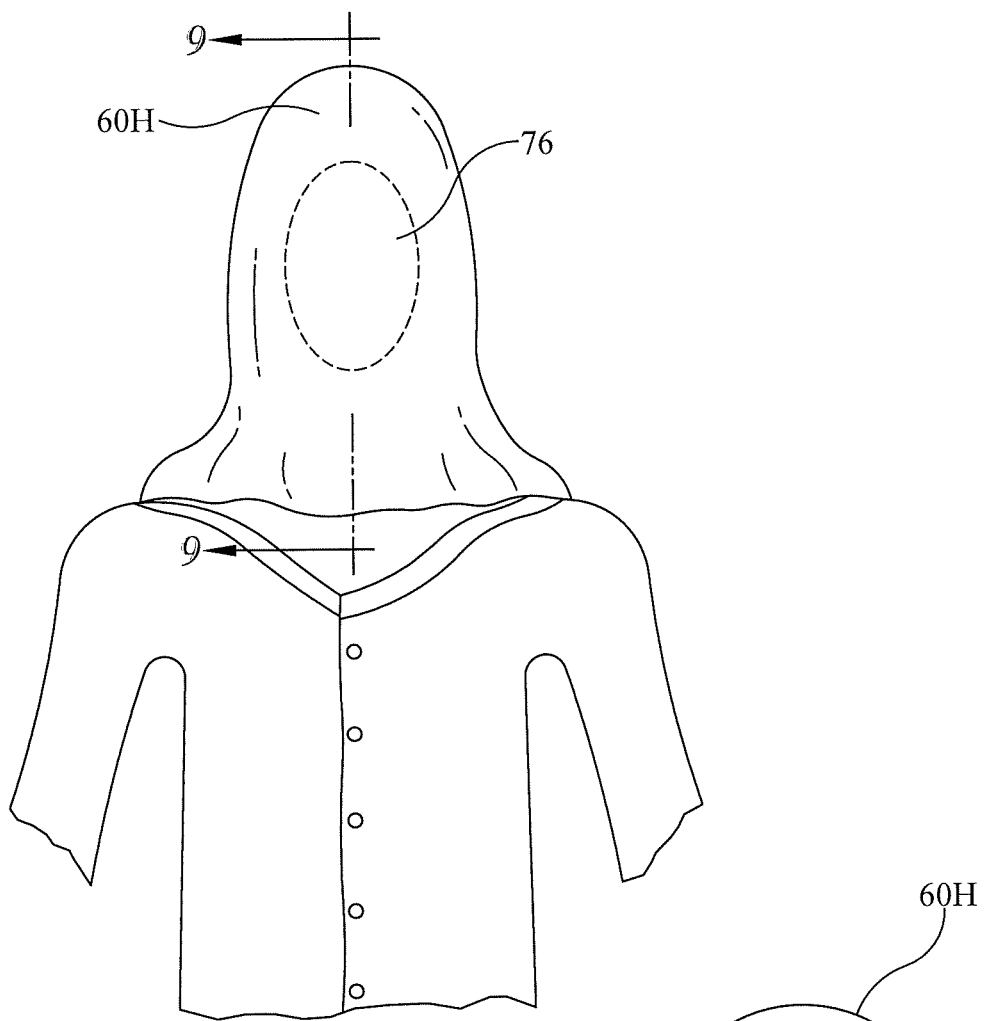
FIG. 8 is a view of a shield component of the eye examination system in which the shield is in the form of a hood which blocks visible light, but at least a portion of which is transparent to infrared wavelengths.
Figure 9:
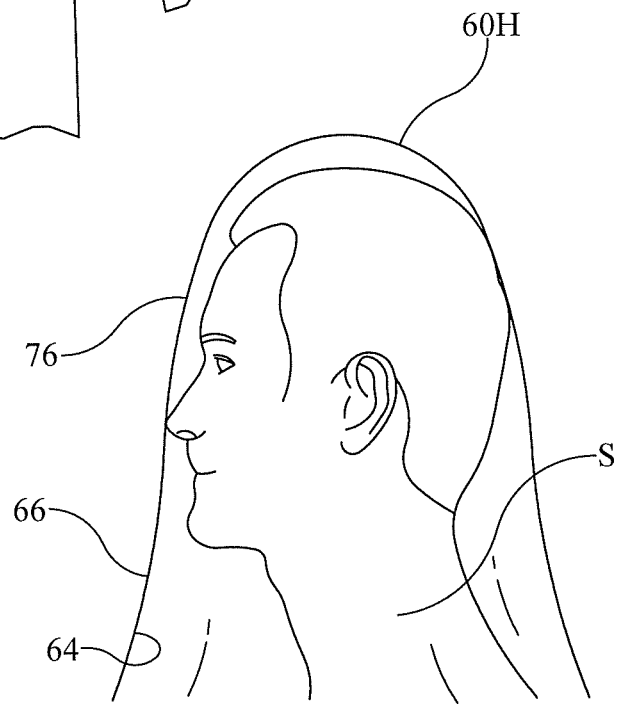
FIG. 9 is a view in the direction 9-9 of FIG. 8.

Referring to FIGS. 8-9, in another embodiment the shield is a hood 60H which is not transparent to visible light. At least a portion 76 of the hood is infrared transparent so that light at infrared wavelengths can propagate from the vision screener to the subject's eyes and vice versa.

Figure 10:
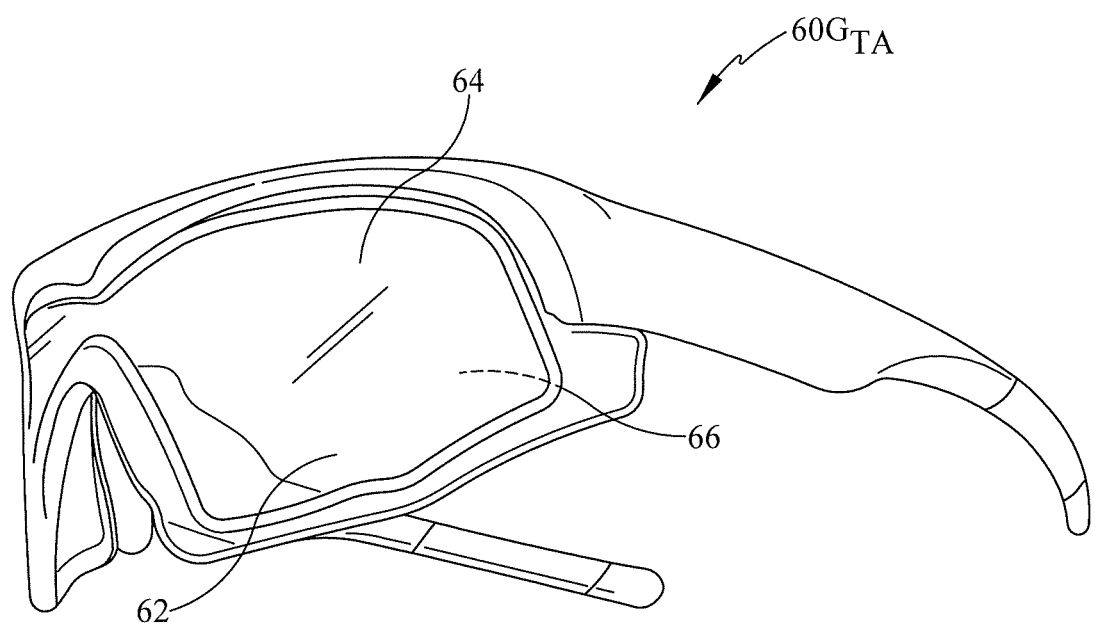
FIG. 10 is a view of a shield component of the eye examination system in which the shield is in the form of tint adjustable glasses.

The shields just described are passive shields in that their transparency or opaqueness to visible wavelengths is fixed, i.e. nonselectable. However irrespective of the exact form of the shield, its transparency to visible wavelengths may be selectable. Such a shield is referred to as an active shield. For example, FIG. 10 shows tint adjustable glasses $60G_{TA}$. The transparency of forward facing portion 62 of glasses $60G_{TA}$ to visible wavelengths is selectable. The glasses can be used in a first operational state, which may alternatively be referred to as an OFF or unpowered operational state, and in a second operational state, which may alternatively be referred to as an ON or powered operational state. If the OFF operational state is selected, the forward facing portion is clear and transparent to both visible and infrared wavelengths. If the ON operational state is selected the forward facing portion rapidly transitions to a tinted operational state which is less transparent to visible wavelengths. Provided that the tinted operational state is infrared transparent and blocks enough visible light to induce a resting state of accommodation, the glasses may be used as shield 60. Tint adjustable glasses which may be suitable as a shield 60 are marketed by AlphaMicron (AMI®) under the trade name e-Tint®.

The tint adjustable glasses may be manually switched between the OFF operational state and the ON operational state. In practice the examiner, or the subject acting on the examiner's instructions, switches the glasses ON prior to the vision screener 22 being operated to carry out the vision examination. With the glasses in the ON operational state the glasses block visible light to induce the required resting state of accommodation for the duration of the examination.

The tint adjustable glasses may also be switched between the ON and OFF operational states by processor 44 acting in accordance with instructions 42. In preparation for the actual examination by infrared wavelengths, the instructions cause the processor to signal the glasses to switch from the OFF operational state of greater transparency to visible wavelengths (less shielding from visible wavelengths) to the ON operational state of less transparency to visible wavelengths (greater shielding from visible wavelengths). In the limit the state of greater transparency is a state of substantially complete transparency, and the state of less transparency is a state of substantially no transparency. With the glasses adjusted to the ON operational state the glasses block visible light to induce the desired resting state of accommodation for the duration of the examination. Once the examination is complete the instructions cause the processor to signal the glasses to switch back to the OFF operational state. Communication between the screener and the tint adjustable shield may be carried out by way of a physical connection or may be carried out wirelessly.

Figure 11:
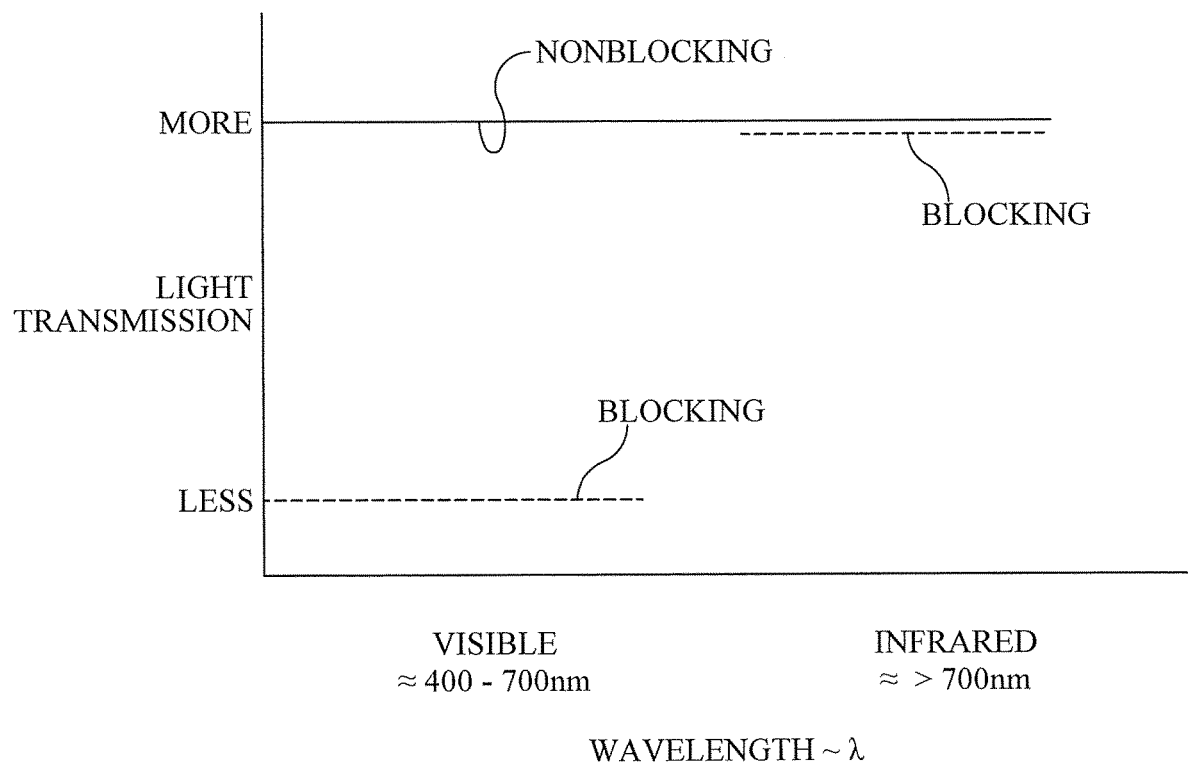
FIG. 11 is a graphical representation showing that the eye examination system has a nonblocking system state which is nonblocking with respect to both visible and infrared wavelengths, and a blocking state which blocks visible wavelengths, but not infrared wavelengths.

Referring to FIG. 11, system 20 has a nonblocking system state (solid line) in which infrared wavelengths generated at the photorefractor can pass through shield 60 and reach the subject's eyes, infrared wavelengths reflected from the subject's eyes can pass through the shield and reach the photorefractor, and visible wavelengths can also reach the subject's eyes. The nonblocking system state corresponds to non-use of a shield such as glasses 60G, pane 60P or hood 60H or to the use of tint adjustable glasses $60G_{TA}$ in the OFF operational state.

System 20 also has a blocking system state (dashed lines) in which infrared wavelengths generated at the photorefractor can reach the subject's eyes, infrared wavelengths reflected from the subject's eyes can reach the photorefractor, and visible wavelengths are blocked from reaching the subject's eyes. The blocking need not be total blocking provided it is sufficient to induce the subject into the desired resting state of accommodation. The blocking system state corresponds to use of a shield such as glasses 60G, pane 60P or hood 60H, or to the use of tint adjustable glasses $60G_{TA}$ in the ON operational state.

Figure 12A:
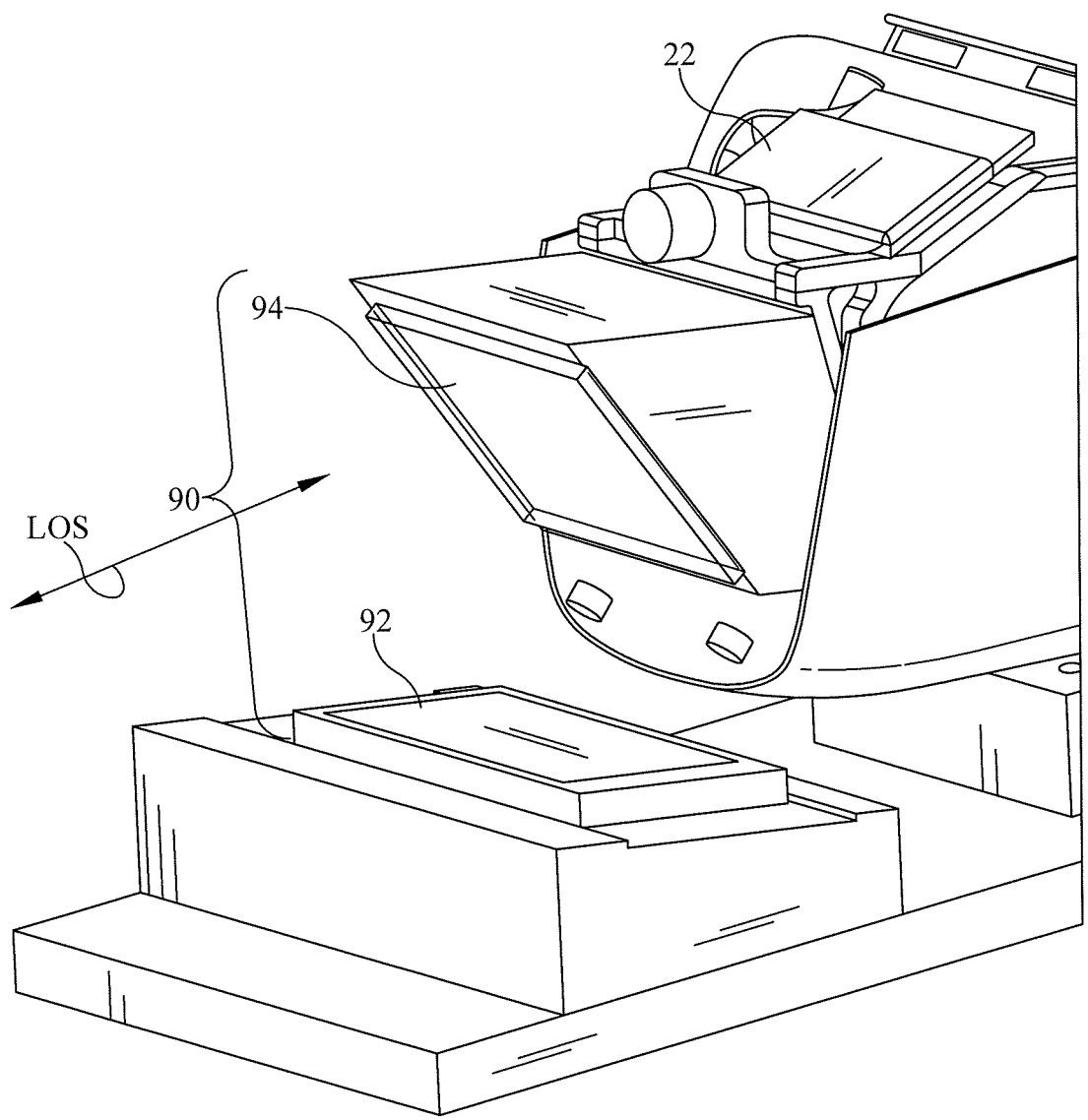
FIG. 12A is a view of an eccentric photorefractor with a barrel portion and other portions of its housing omitted to reveal selected internal components which include an image source and an image display element.

FIG. 12A shows an eccentric photorefractor 22 with its barrel and other portions of its housing omitted to reveal selected internal components. The illustrated photorefractor includes a display system 90. The illustrated display system includes an image source or generator 92 such as a liquid crystal display (LCD) which is not in the line of sight LOS between the subject and the photorefractor. The photorefractor also includes an image display element 94 affixed to the inside of the barrel, which is not shown. The illustrated display element is an obliquely oriented panel of glass. The glass panel is transparent to infrared wavelengths so that infrared light can propagate from the vision screener to the subject's eyes and vice versa. The glass panel reflects visible light from LCD 94 toward the subject so that an image originating at the image source is introduced into the subject's line of sight to the photorefractor 22.

Figure 13:
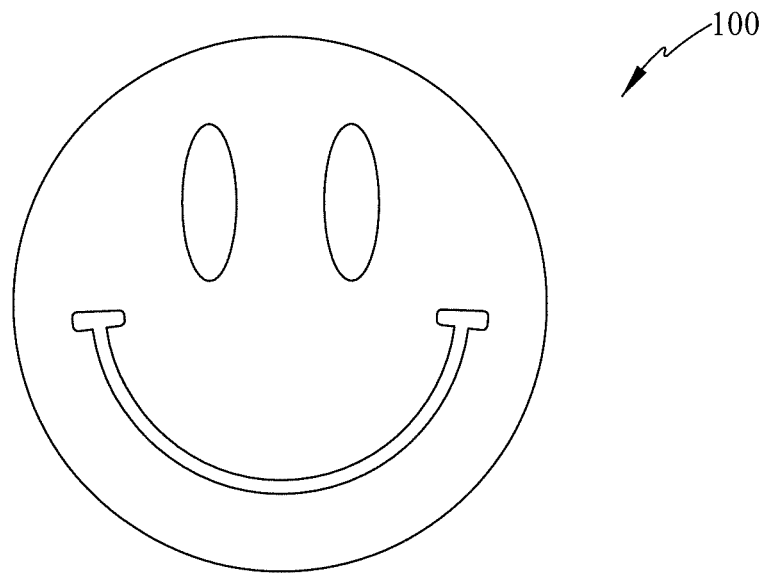
FIGS. 13 and 14 are relaxing or comforting images used in one embodiment of the eye examination system.
Figure 14:
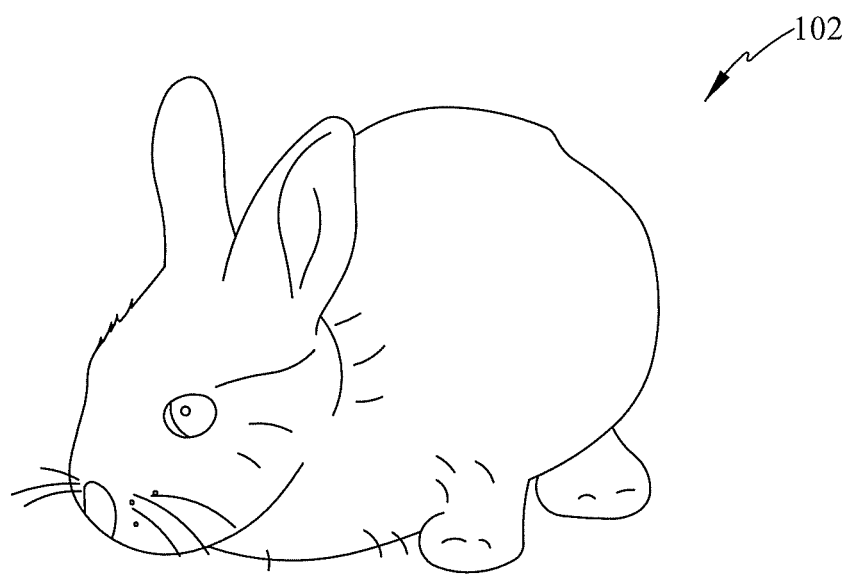

Photorefractor 22 and a shield 60 (not illustrated in FIG. 12A) are elements of a system for conducting a vision examination. In practice, before the system of FIG. 12A enters the blocking state (or is placed into the blocking state by a user) image generator 92 generates a comforting image. The display element 94 reflects the image toward the subject. Examples of a comforting image include a smiley face 100 (FIG. 13) and a bunny 102 (FIG. 14). The image may be a sharp image, as shown, or may be an out of focus (blurred) or fogged image. The comforting image may help the subject relax, thereby causing some dilation of his pupils and improving his ability to maintain the desired resting state of accommodation during the subesequent time interval of operation in the blocking state. The relaxing image is turned off before the onset of the examination with infrared light, otherwise the subject's eyes would likely remain fixed on the image rather than being in the resting state of accommodation.

Figure 12B:
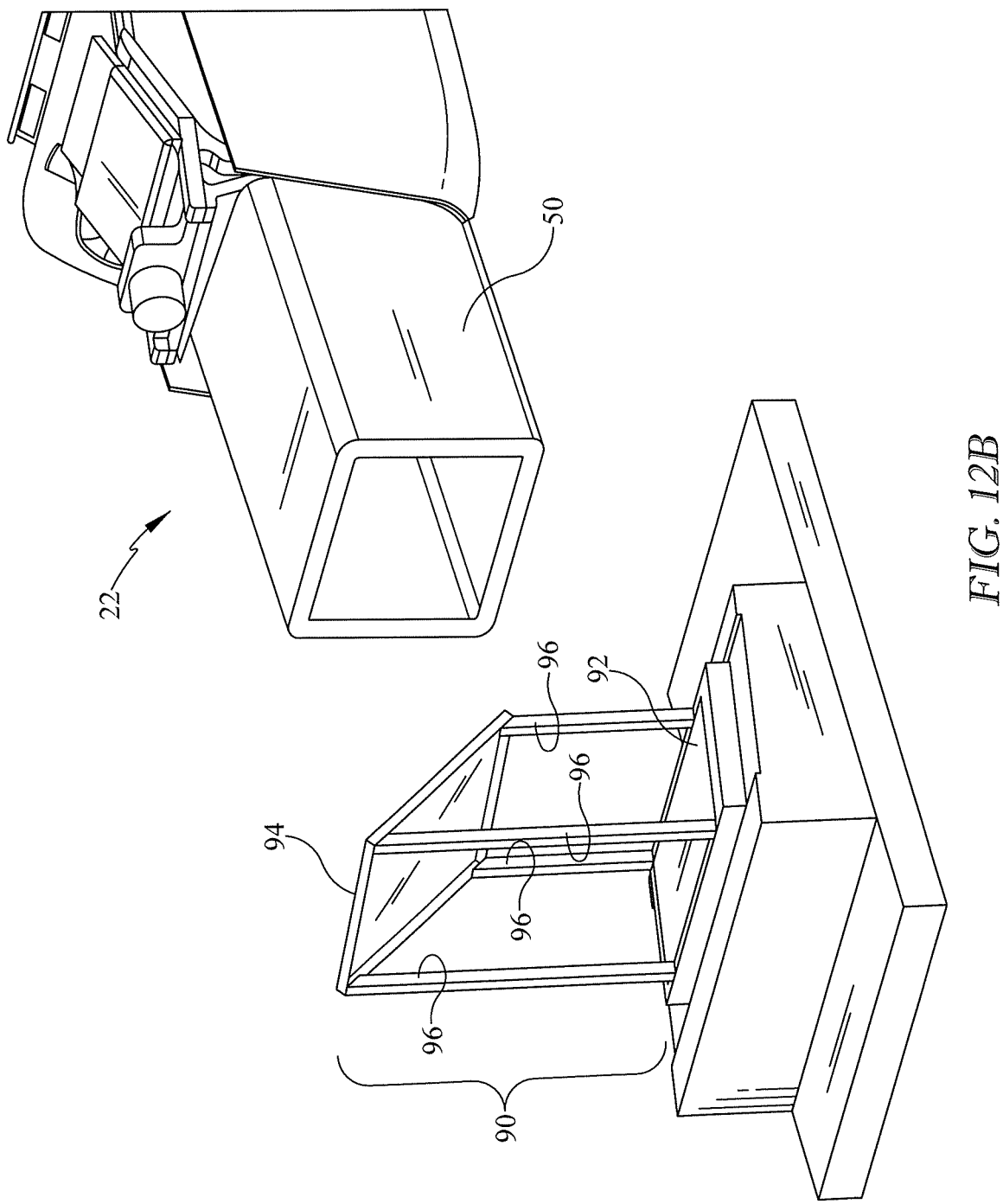
FIG. 12B is a view similar to FIG. 12A with the housing of the eccentric photorefractor illustrated and the image source and an image display element shown as a stand-alone display system.

FIG. 12A shows display system 90 integrated into the eccentric photorefractor. Alternatively the display system could be a stand-alone system as seen in FIG. 12B. The system includes posts 108 to hold display element 94 a sutable distance away from image source 92.

Figure 15:
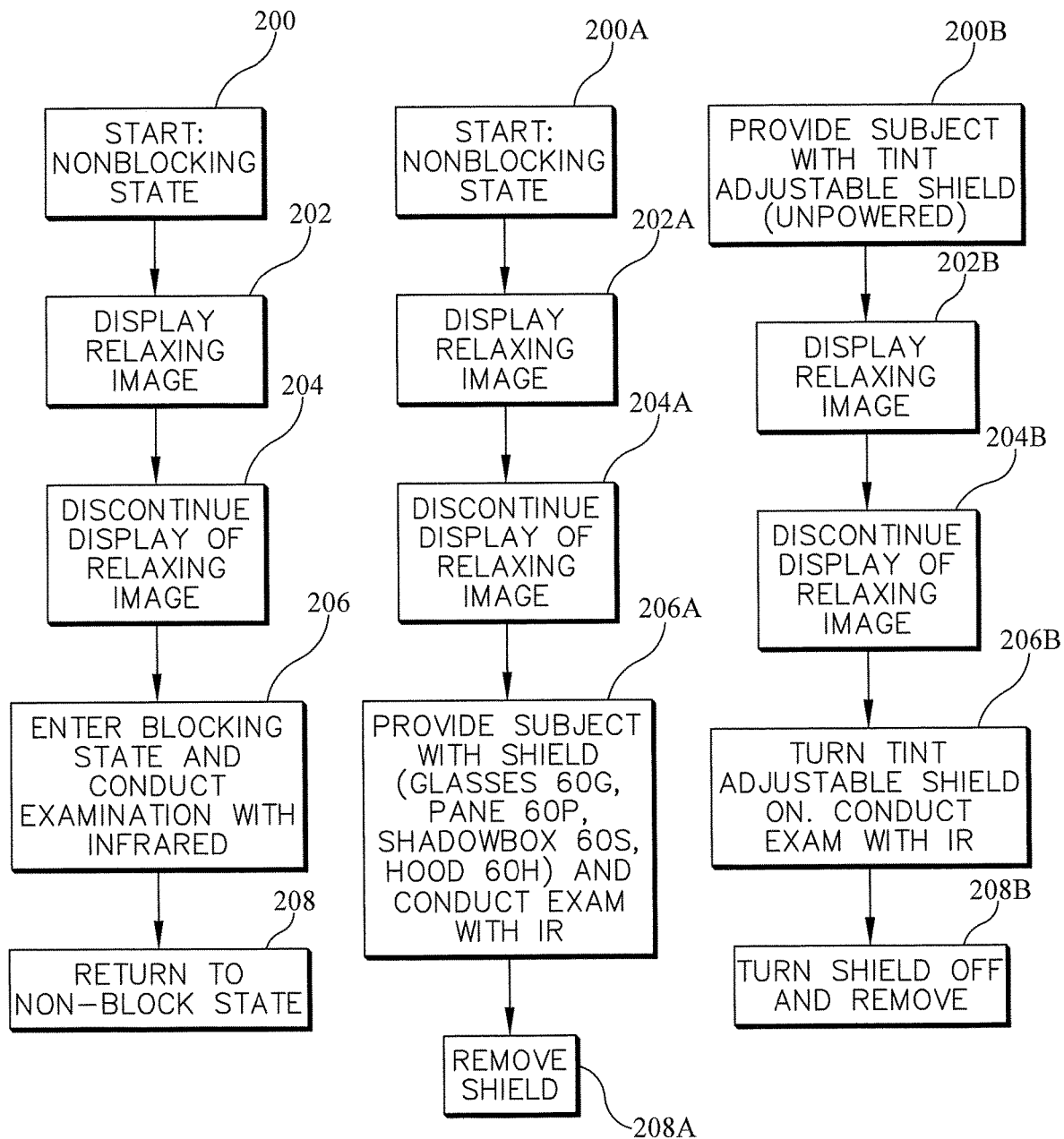
FIG. 15 is a set of flow charts showing operation of the eye examination system in general terms, in connection with a passive shield, and in connection with an active shield.

FIG. 15 is a set of flow charts arranged side by side to show operation of the eye examination system, and an associated method of eye examination in general terms, in connection with a passive shield, and in connection with an active shield. Block 200 represents the nonblocking state of the eye examination system. That is, the subject's eyes are not shielded from visible light. At block 202 a comforting or relaxing image is displayed to the subject. At block 204 the display of the image is discontinued. Block 206 represents entry into the blocking state in which the subject's eyes are shielded from visible light, and conduct of the actual examination with infrared light. Block 208 shows a return to the nonblocking state of the system.

Continuing to refer to FIG. 15, the blocks numbered with an "A" suffix are analogous to the blocks just described, but are in the specific context of a passive shield. At block 206A, entry of the system into the blocking state involves providing the subject with a shield such as glasses 60G, pane 60P of material, hood 60H, or shadowbox 60S. At block 208A, return to the nonblocking state involves removal of the shield, i.e. the subject removes the glasses 60G or hood 60H or sets aside pane 60P of material or discontinues use of shadowbox 60S.

Continuing to refer to FIG. 15, the blocks numbered with an "B" suffix are analogous to the blocks just described, but are in the specific context of an active shield. At block 200B, the subject is provided with a tint adjustable shield, such as glasses $60G_{T4}$, in its unpowered operational state (nonshielding with respect to visible wavelengths). At block 206B, entry of the system into the blocking state involves selecting the powered or shielding operational state of the shield. At block 208B return to the nonblocking state involves deselecting the shielded state of the shield, e.g. glasses $60G_{T4}$ to return to the nonshielded state and removing the glasses from the subject.

The steps of displaying and discontinuing the display of an image at blocks 202, 202A, 202B, 204, 204A, and 204B are optional.

A method of conducting an eye examination on a subject includes the step of providing a shield 60. At least part of the provided shield is transparent to infrared wavelengths. The shield blocks visible wavelengths enough that when the shield is used, the subject experiences a condition of darkness sufficient to promote the desired resting state of accommodation. Suitable forms of the shield are glasses, a flat or curved pane of material, a hood, and a shadowbox, examples of all of which are described below.

Figure 16:
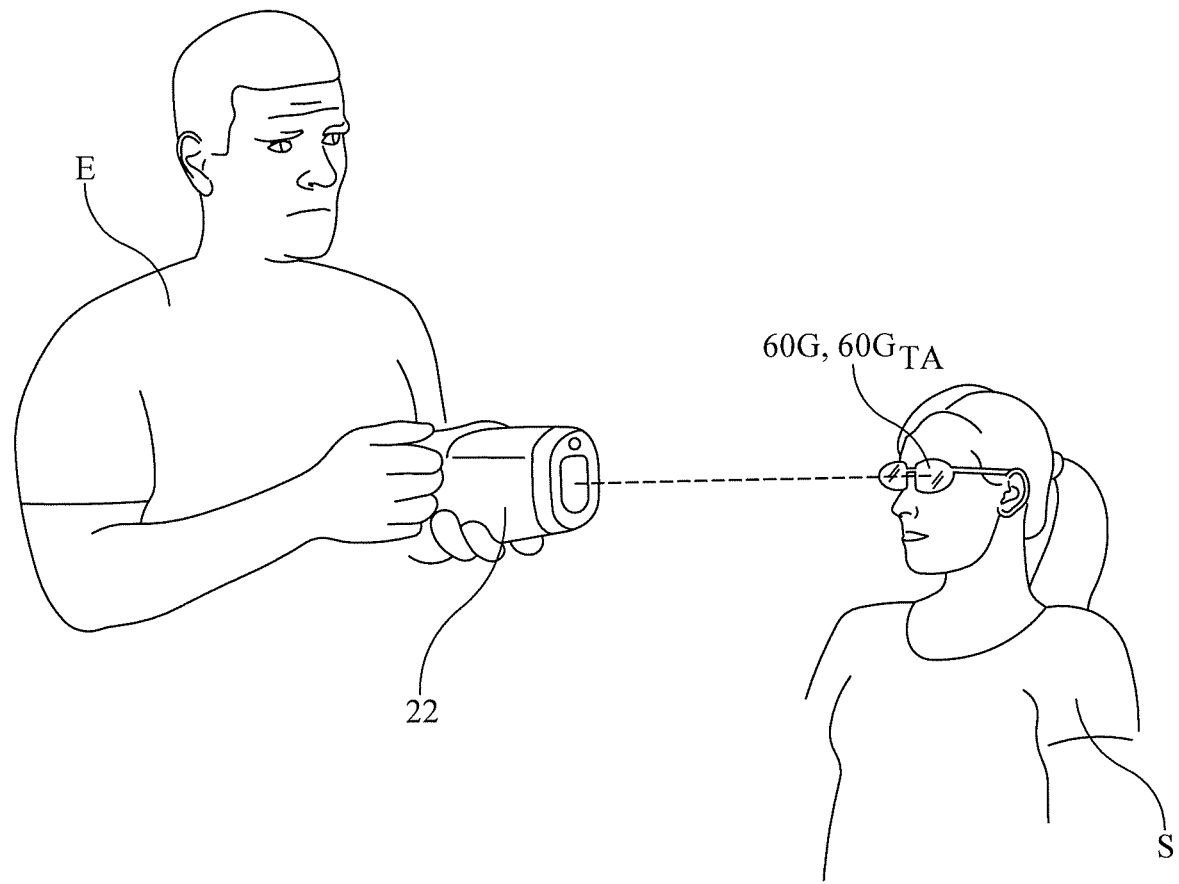
FIGS. 16, 17, and 18 are views similar to FIG. 5 showing an eye examination being conducted with the eye examination system described herein and in which the shield component of the system is, respectively, a pair of passive glasses, a hand held pane of material, and a pane of material supported by a stanchion.

FIG. 16 shows a subject who has been provided with a shield in the form of dark glasses 60G or $60G_{T4}$ and has put the glasses on. The provided glasses are positioned between the subject's eyes and the examination instrument 22.

Figure 17:
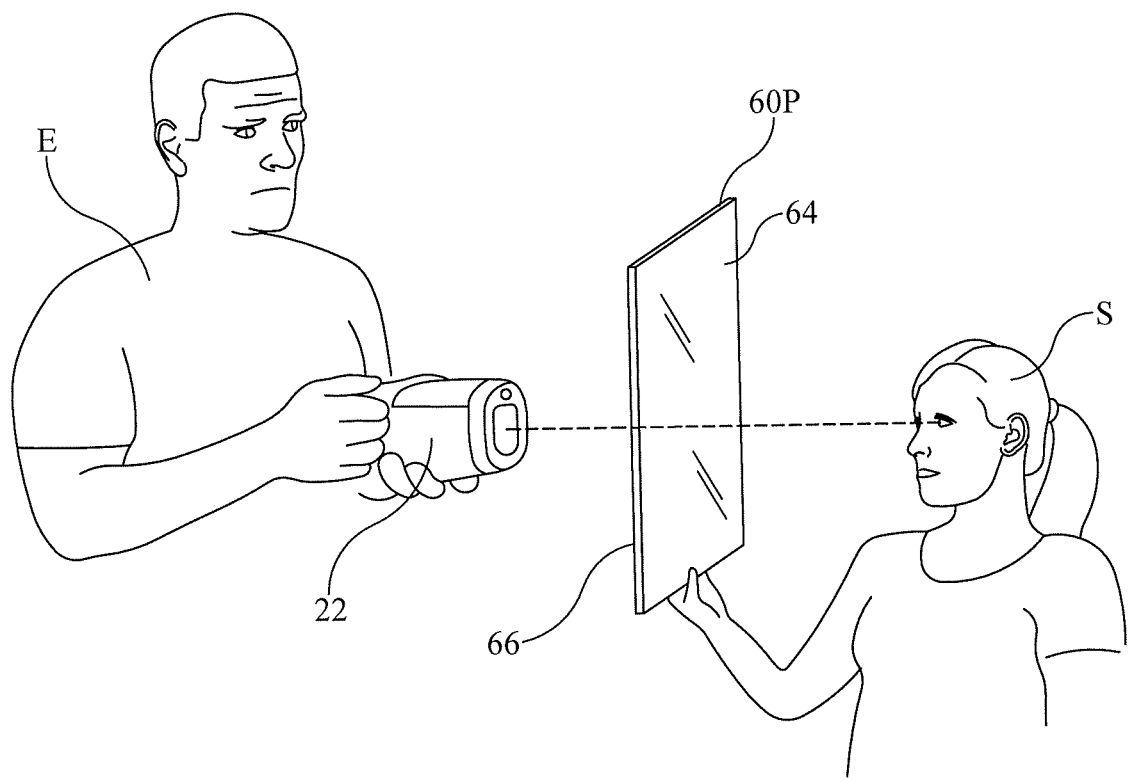
Figure 18:
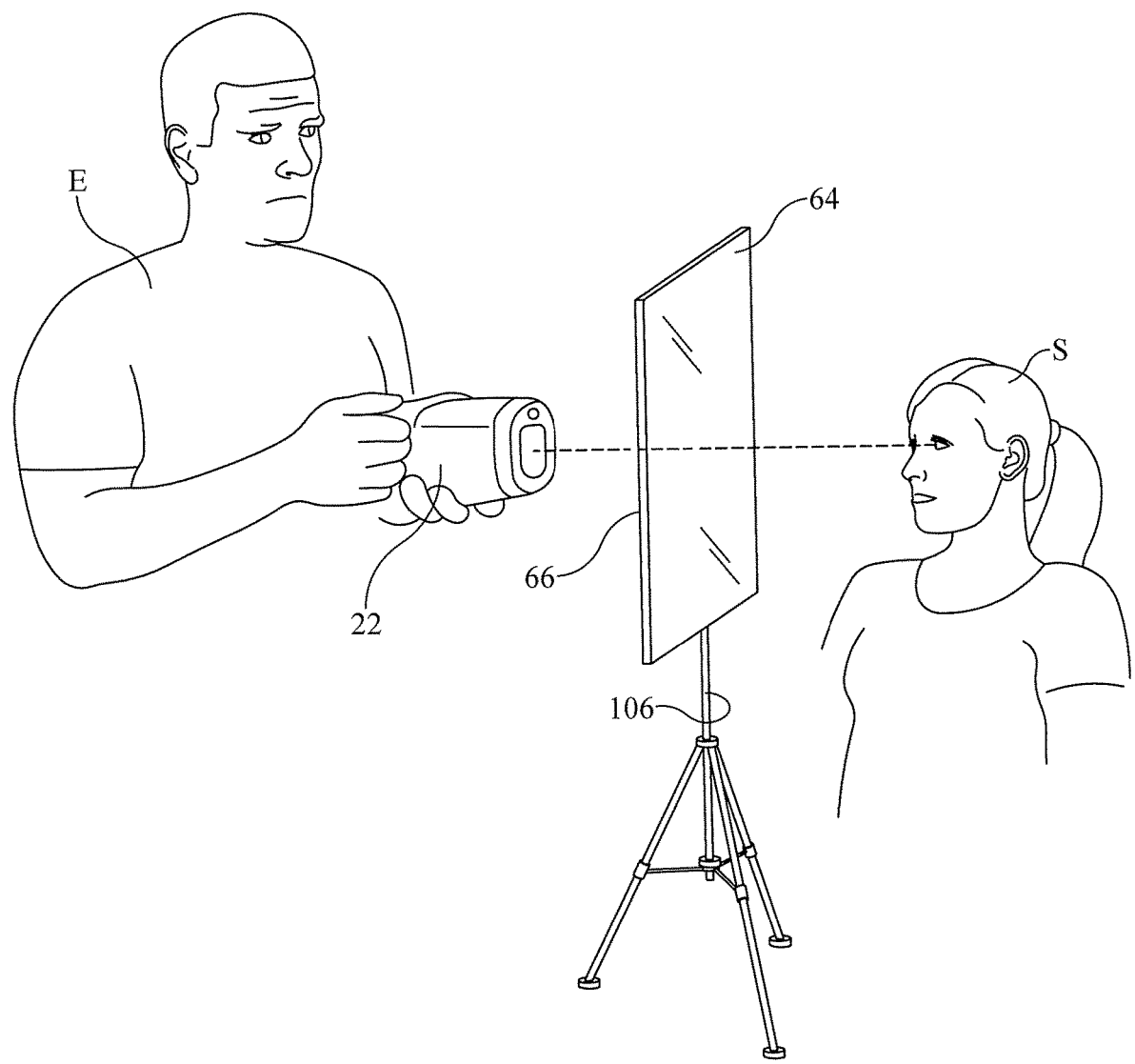

FIGS. 17-18 show a subject who has been provided with a shield in the form of a flat pane 60P of material. Although the illustration shows a flat pane, the pane can be curved in two or three dimensions to better shield the subject's eyes from ambient light. In FIG. 17 the subject is holding the shield close to his face. In FIG. 18 the shield is independently supported, e.g. by stanchion 106, and the subject has positioned his face next to the subject facing side of the shield. Either way the pane of material has been provided to the subject, and is positioned between the subject's eyes and the examination instrument 22.

FIG. 7D shows a subject who has been provided with a shield in the form of a shadowbox 60S. The subject has positioned his face slightly past plane P so that his eyes are sufficiently shielded from visible light to induce the desired resting state of accommodation.

FIGS. 8-9 show a subject who has been provided with a shield in the form of a hood and who has put the hood on. The front of the provided hood is positioned between the subject's eyes and the examination instrument 22.

The method also includes carrying out the examination with an instrument having an illumination source which emits light at the infrared wavelengths to which the shield is transparent. One example of a suitable instrument is an eccentric photorefractor. The examination is carried out with the instrument located on the examiner facing side of the shield and the subject's eyes on the subject facing side of the shield.

In one embodiment the method includes the step of showing the subject a comforting image prior to shielding the subject's eyes from visible light, as already described in connection with FIGS. 12A and 12B. Examples of relaxing images include smiley face 100 (FIG. 13) and bunny 102 (FIG. 14). The image may be displayed on an image display element, such as element 94 of FIG. 12A or 12B, which is in the subject's line of sight to the vision evaluation instrument and which is also between the subject and the instrument 22. Alternatively, the relaxing image may be a physical prop such as a smiley face printed on a sheet of paper or a stuffed toy bunny.

Figure 19:
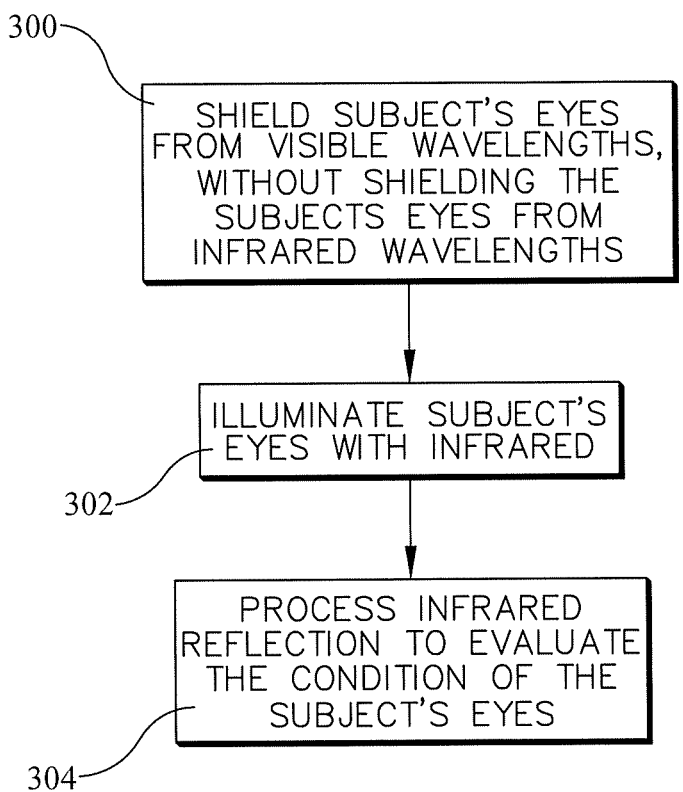
FIG. 19 is a block diagram of a method of examining a subject's eyes.

FIG. 19 is a block diagram showing the method of examining a subject's eyes. At block 300 the method includes the step of shielding the subject's eyes from visible wavelengths of light without shielding the subject's eyes from infrared wavelengths. At block 302 the method includes the step of illuminating the subject's eyes with infrared light. At block 304 the method includes the step of processing infrared light reflected from the subject's eyes as a result of the illumination to evaluate the condition of the subject's eyes.

Referring back to FIG. 6A, the purpose of watermark 78 can now be better appreciated. The watermark is an imprint that blocks selected infrared wavelengths that are expected to be encountered during use of the eye examination system 20. For example, shield portion 62 of glasses 60G may be designed to block wavelengths below 750 nm (visible light) and to pass wavelengths in the 750 to 1500 nm portion of the infrared spectrum. However the watermark is designed to block wavelengths greater than 850 nm and therefore appears as an infrared dark spot to photorefractor 22. The presence of the infrared dark spot informs the processor that a shield 60 is in use. As a result, the subroutines or subsets of instructions that are applicable to the use of a shield 60 are executed. Conversely, if the dark spot is absent the subroutines or subsets of instructions that are applicable to non-use of a shield 60 are executed. As noted previously, use of the shield is not necessary when the eye examination is conducted under well controlled conditions.

As explained above the step of shielding the subject's eyes includes providing a shield. This differs from methods that involve darkening an examination room by turning off or significantly dimming the room lights. Turning off or dimming lights removes a stimulus (ambient visible light) from the subject's surroundings, or attenuates the stimulus. By contrast, the step of shielding the subject's eyes permits that influence to be present in the surroundings, but prevents it from arriving at the subject's eyes.

Figure 20:
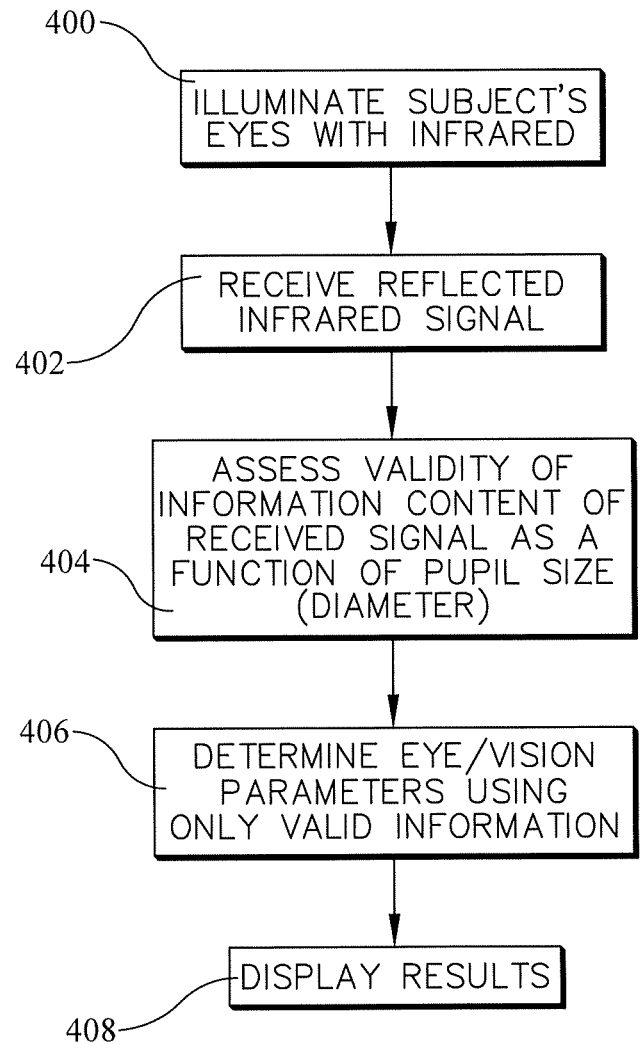
FIG. 20 is a block diagram of a method of examining a subject's eyes which determines eye and/or vision related parameters using only information which is considered to be valid.

The methods described above seek to ensure accuracy of the eye examination by attempting to force the subject into a resting state of accommodation. FIG. 20 shows a method which can be used independently of the "forced" method or can be used in conjunction with the forced method in order to further improve its accuracy.

At block 400 the method illuminates the subject's eyes with light at infrared wavelengths. At block 402 the method receives infrared radiation reflected from the subject's eyes.

At block 404 the method assesses the validity of the information content of the reflected infrared signal. The assessment is based on the knowledge that when the subject is in the desired resting state of accommodation, the diameter of his pupils is greater than when he is not in the resting state of accommodation. Therefore, the information content of the reflected signal corresponding to time intervals when pupil diameter is below a threshold diameter is considered to lack validity and is disregarded. Conversely, the information content of the reflected signal corresponding to time intervals when pupil diameter is greater than the threshold is considered to be valid information. (The case where pupil diameter equals the threshold can be included in either the valid or the nonvalid category as specified by the system designer.)

At block 406, only the valid information is used by the photorefractor processor 44 to determine the optical parameters of interest. At block 408 the method displays the results of the examination.

The method may use more finely graduated estimates of validity than the valid/nonvalid categorization just described. In general the method may use N thresholds to define N+1 categories of validity. To the extent that information other than that considered to be of the highest validity is used in the determination of the subjects eye and vision parameters, processor 44 can assign a validity score to the examination results and report that score at block 408. In the limit, the processor can use all the information content of the reflected infrared signal (or all the content corresponding to at least a minimum pupil diameter which, in the limit, can be zero) and, based on the variation in pupil diameter during the examination, assign a validity score to the examination results. In the limit case just described all the data used by the processor is considered to have some degree of validity, however some of the information content is of higher validity while some is of lower validity.

The examination validity score need not be the same for all the parameters determined by processor 44 at block 406. Instead, different parameters can be assigned different scores depending on how the accuracy of each parameter is believed to be affected by the subject's eyes not being in the resting state of accommodation, as indicated by pupil diameter.

Figure 21:
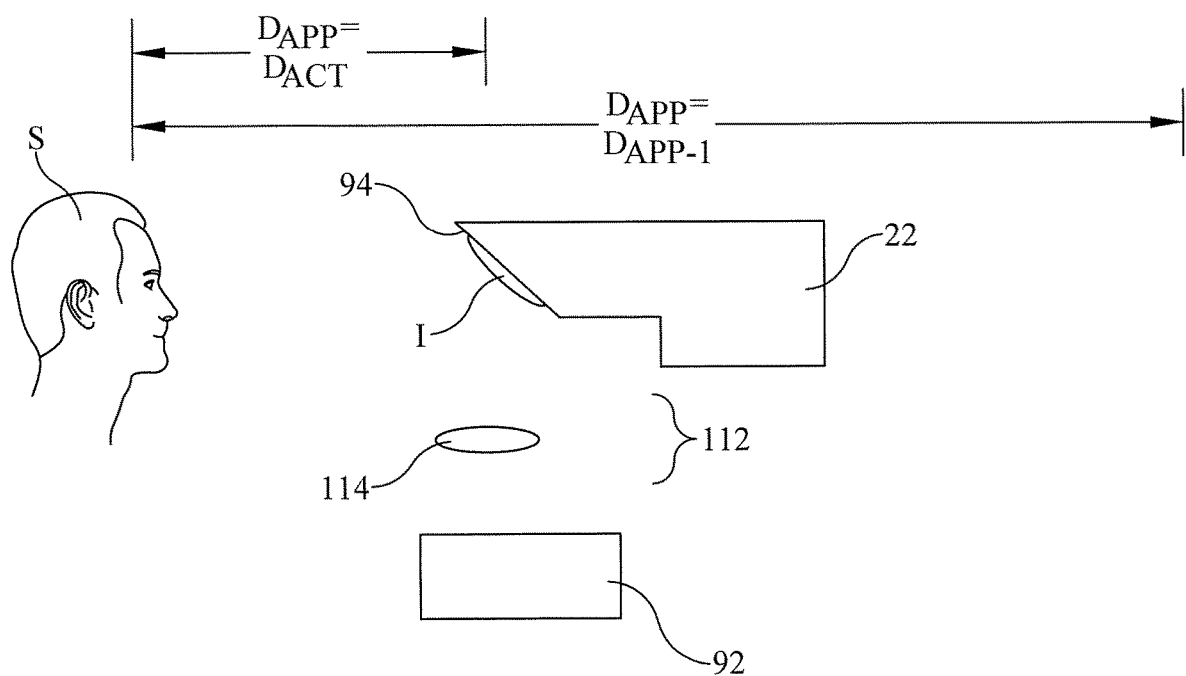
FIG. 21 is a schematic view of a system similar to that of FIGS. 12A and 12B but including an image adjusting subsystem in the form of a lens.

FIG. 21 shows another system for carrying out an eye examination. The system of FIG. 20, like that of FIGS. 12A and 12B includes an instrument 22 which emits light at a wavelength or in a range of wavelengths suitable for the eye examination. One example is the photorefractor vision screener of FIG. 12A or 12B and the infrared wavelengths emitted by those photorefractors. The system of FIG. 21 also includes an image source 92 and an image display element 94, both of which are analogous to the image source and image display element of FIGS. 12A and 12B. The system also includes an image adjusting subsystem 112. The system does not include a shield 60 as described in connection with previously described embodiments.

Image adjusting subsystem 112 is configured to adjust the apparent distance $D_{APP}$ between subject S and image I to a distance other than the actual distance $D_{ACT}$. For example if image adjusting subsystem 112 were not present, the apparent distance $D_{APP}$ between the subject and the image would be the same as the actual distance $D_{ACT}$. With the image adjustment subsystem present the apparent distance $D_{APP-1}$ is greater than $D_{ACT}$. Distance $D_{APP-1}$ is a distance that encourages the subject to maintain a resting state of accommodation. Image I need not be a relaxing or comforting image but in practical embodiments would likely not be a disturbing image.

An associated method of conducting an eye examination includes the step of providing an instrument having an illumination source which emits at a wavelength or wavelengths suitable for the eye examination. In one example infrared wavelengths are employed. The method also includes the step of displaying an image to the subject so that the subject perceives the image to be further away than is actually the case. In other words the image is at an apparent distance from the subjects eyes which differs from its actual distance from the subject's eyes. In one example the apparent distance is a distance which induces a resting state of accommodation. The method also includes the step of carrying out the examination in the presence of the image.

In the embodiment of FIG. 21 the image adjusting subsytem is a single lens 114. The lense is selected to make image I appear far away in order to induce a resting state of accommodation.

Figure 22:
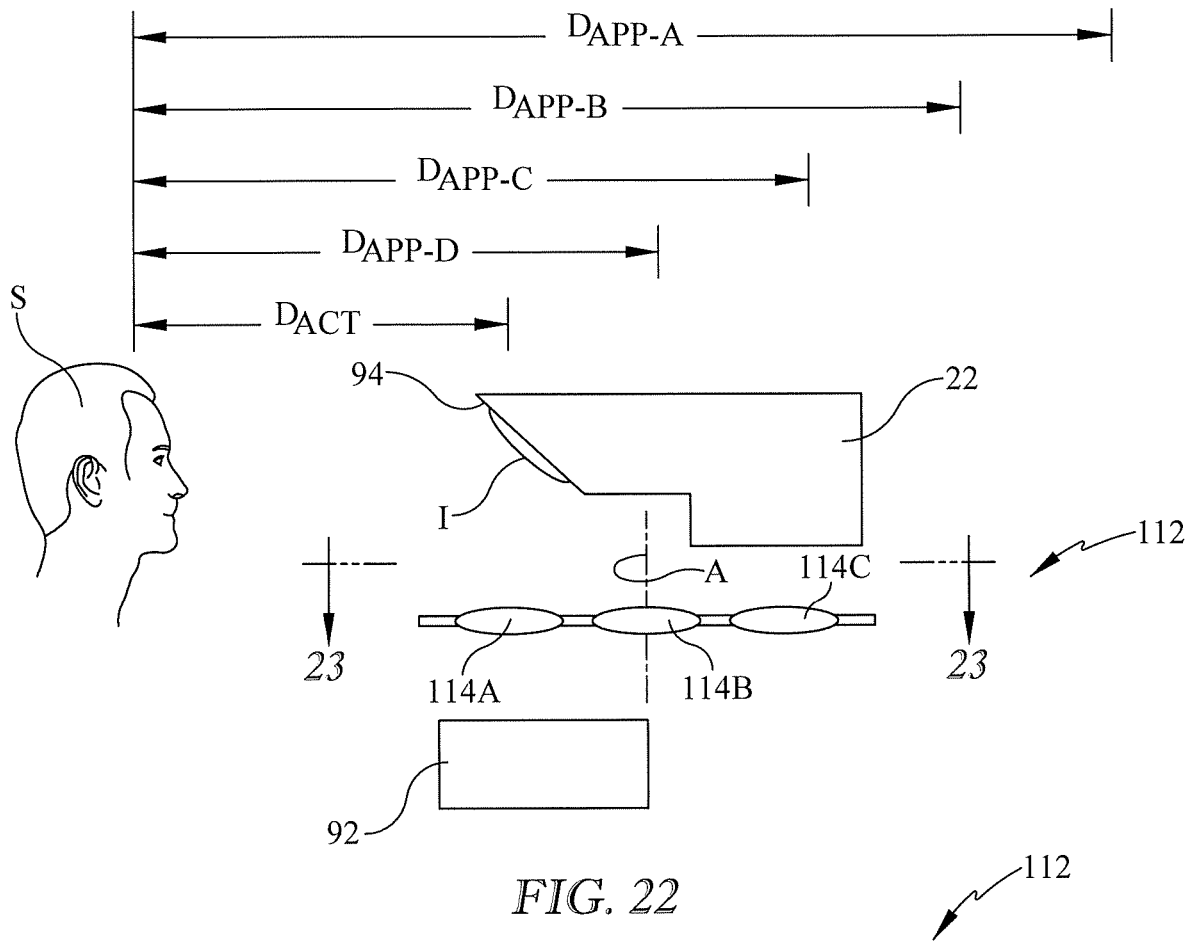
FIG. 22 is a view similar to FIG. 21 including multiple lenses held in a carousel.
Figure 23:
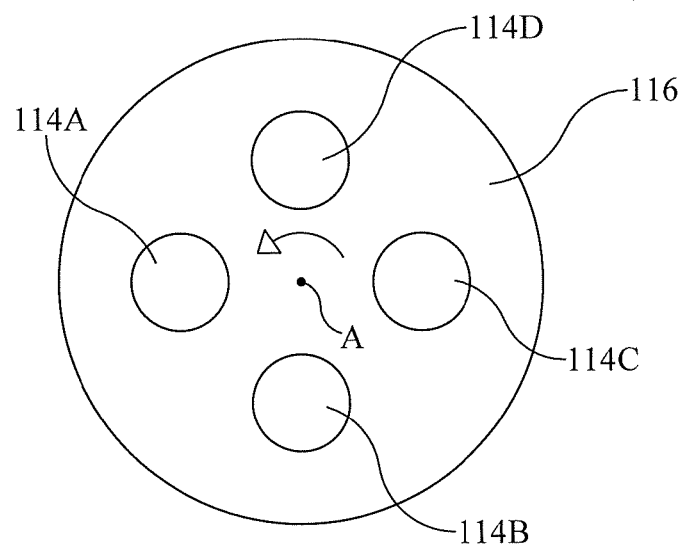
FIG. 23 is a view in the direction 23-23 of FIG. 22 showing a plan view of the carousel.

FIGS. 22-23 show an embodiment in which image adjusting subsystem 112 includes a carousel 116 which is rotatable about axis A. The carousel holds two or more lenses, for example lenses 114A, 114B, 114C and 114D. By rotating the carousel to select which of the multiple lenses is between image source 92 and image display element 94, a user can adjust the apparent distance to distances $D_{APP-A}$, $D_{APP-B}$, $D_{APP-C}$, or $D_{APP-D}$.

In practice the examiner displays an image to the subject using lens 114A so that the subject perceives the image to be at apparent distance $D_{APP-A}$. The examiner carries out the examination in the presence (as perceived by the subject) of the image at apparent distance $D_{APP-A}$. The examiner then rotates the carousel to bring lens 114B between image source 92 and image display element 94. As a result the subject perceives the image to be at apparent distance $D_{APP-B}$. The examiner carries out the examination in the presence (as perceived by the subject) of the image at apparent distance $D_{APP-B}$. The examiner then repeats the actions of displaying a false distance image to the subject and carrying out an examination two more times, once with lens 114C and an apparent distance of $D_{APP-C}$, and once with lens 114D and an apparent distance of $D_{APP-D}$.

The examiner, or instructions executed by processor 44, then estimates one or more vision related parameters of interest as a function of the results of the examinations carried out with lenses 114A through 114D at apparent distances $D_{APP-A}$ through $D_{APP-D}$.

In view of the foregoing the reader can now appreciate that the eye examination systems and associated methods described herein achieve the goal of enabling an examiner to carry out an accurate vision examination in environments which are not well controlled and in which the subject may be unable or unwilling to maintain the desired resting state of accommodation for the duration of the examination. The devices and methods may be particularly advantageous for examinations conducted in poorly controlled environments such as a high visible light environment or a noisy environment.

Although this disclosure refers to specific embodiments, it will be understood by those skilled in the art that various changes in form and detail may be made without departing from the subject matter set forth in the accompanying claims.

We claim:

1. A system for conducting an examination of the eyes of a subject, comprising:
   an examination instrument which emits light at infrared wavelengths; and
   a shield, at least a portion of which is transparent to the emitted infrared wavelengths and which provides shielding of the subject's eyes from visible wavelengths.

2. The system of claim 1 wherein the shield is a pair of glasses.

3. The system of claim 1 wherein the shield is a pane of material.

4. The system of claim 1 wherein the shield is a hood.

5. The system of claim 1 wherein the shield is a shadowbox having top, bottom, left and right panels which provide the shielding from visible wavelengths and having a rearward panel which provides the transparency to the emitted infrared wavelengths.

6. The system of claim 1 wherein the shield includes a mark which is not transparent to a subspectrum of the infrared wavelengths.

7. The system of claim 1 wherein the shielding from visible wavelengths is selectable.

8. The system of claim 7 comprising a processor for executing machine readable instructions, and wherein the processor selects or deselects the shielding from visible wavelengths in response to the instructions.

9. The system of claim 8 wherein the processor, operating in response to the instructions, carries out the steps of:
   a) signaling the shield to transition from a first state of less shielding from visible wavelengths to a second state of greater shielding from visible wavelengths; and
   b) operating the examination instrument after completion of the signaling step.

10. The system of claim 9 comprising:
    c) signaling the shield to transition from the second state to the first state after completion of the operating step.

11. The system of claim 1 wherein the system includes:
    an image source which is not in the line of sight between the subject and the instrument; and
    an image display element which is in the line of sight between the subject and the instrument.

12. The system of claim 1 wherein the examination instrument includes:
    an image source which is not in the line of sight between the subject and the instrument; and
    an image display element which is in the line of sight between the subject and the instrument.

13. A method of conducting an eye examination on a subject comprising:
    providing a shield which is transparent to infrared wavelengths but nontransparent to visible wavelengths, the shield having a subject facing side and an examiner facing side; and
    carrying out the examination with an instrument which is located on the examiner facing side of the shield, the instrument having an illumination source which emits at the infrared wavelengths to which the shield is transparent.

14. The method of claim 13 wherein the instrument is an eccentric photorefractor.

15. The method of claim 13 wherein the shield is a pair of glasses.

16. The method of claim 13 wherein the shield is a pane of material.

17. The method of claim 13 wherein the shield is a hood.

18. The method of claim 13 comprising displaying a relaxing image to the subject before the step of carrying out the examination.

19. The method of claim 18 wherein the relaxing image is an image introduced into the subject's line of sight to the instrument.

20. The method of claim 11 including a display system for introducing an image into the subject's line of sight to the instrument.

21. The method of claim 11 wherein the instrument is an eccentric photorefractor which includes:
    an image source which is not in the line of sight between the subject and the instrument; and
    an image display element which is in the line of sight between the subject and the instrument.

22. The method of claim 11 wherein the nontransparency of the shield to visible wavelengths is selectable.

* * * * *